US006727075B2

(12) United States Patent
Fitzgerald et al.

(10) Patent No.: US 6,727,075 B2
(45) Date of Patent: Apr. 27, 2004

(54) METHODS AND COMPOSITIONS FOR DETERMINING LIPID PEROXIDATION LEVELS IN OXIDANT STRESS SYNDROMES AND DISEASES

(75) Inventors: Garret A. Fitzgerald, Wayne, PA (US); Joshua Rokach, Satellite Beach, FL (US); Domenico Pratico, Philadelphia, PA (US); John Q. Trojanowski, Philadelphia, PA (US)

(73) Assignees: The Trustees of the University of Pennsylvania, Philadelphia, PA (US); Florida Institute of Technology, Melbourne, FL (US)

( * ) Notice: Subject to any disclaimer, the term of this patent is extended or adjusted under 35 U.S.C. 154(b) by 0 days.

(21) Appl. No.: 09/870,762

(22) Filed: May 31, 2001

(65) Prior Publication Data

US 2002/0072083 A1 Jun. 13, 2002

Related U.S. Application Data

(63) Continuation of application No. PCT/US99/28583, filed on Dec. 2, 1999.
(60) Provisional application No. 60/110,569, filed on Dec. 2, 1998.

(51) Int. Cl.$^7$ ............................................... C12Q 1/26
(52) U.S. Cl. .......................................... 435/25; 435/7.1
(58) Field of Search .................... 435/25, 7.1; 424/9.2; 436/811

(56) References Cited

U.S. PATENT DOCUMENTS

| | | | |
|---|---|---|---|
| 5,700,654 A | * 12/1997 | Roberts et al. | ................ 435/25 |
| 5,858,696 A | 1/1999 | Roberts, II et al. | |
| 5,891,622 A | * 4/1999 | Morrow et al. | ................ 435/4 |
| 5,945,295 A | 8/1999 | Roberts, II et al. | |

FOREIGN PATENT DOCUMENTS

WO    WO 94/04921    * 3/1994

OTHER PUBLICATIONS

Pratico, D. Increased 8, 12–iso–iPF2aVI in AD. Ann Neurol 2000:48:809–812.*
Rokach J. Isoprostanes: Chemistry and Biological Significance. Recent Res Devel in Organic Chem 1998, vol. 2, pp. 393–407.*
Mardini I. A Newly Discovered Isoprostane is a Marker of Oxidative stress in LPS Mediated Inflammation in Humans. Circulation Oct. 27, 1998, 98 (17 Sup) p. 17.*
Pratico D. Faseb J Increased F2 Isoprostanes in AD. 1998 12(15)1777–1783.*
Reilly M. Circulation. Increased Formation of Distinct F2 Isoprostanes in Hypercholesterolemia. 1998 98(25)2822–28.*
Fitzgerald G. Faseb J. Isoprostanes: Indices of Oxidant Stress. 1996 10(6)A1138.*
Pratico D. Noval Indices of Oxidant Stress in Cardiovascular Disease: Specific Analysis of F2 Isoprostanes. Prostaglandins and Control of Vascular Smooth Muscle Cell Proliferation. 1997 vol. 48, pp. 25–41.*
Arai, et al., 1995, Ann. Neurol. 38:649–652.
Arnold, et al., 1995, Am. J. Psych. 152:731–737.
Awad, et al., 1993, J. Biol. Chem. 268:4161–4169.
Balazs et al., 1994, Neurochemical Research 19:1131–1137.
Banerjee et al., 1992, Amer. Physiological Society H660–H663.
Behl, et al., 1994, Cell 77:817–827.
Busciglio, et al., 1995, Neuron. 14:879–888.
Corder, et al., 1993, Science 261:921–923.
Delanty, et al., 1997, Circulation 95:2492–2499.
Gutteridge, et al., 1990, Trends Biochem Sci. 15:129–135.
Hardy, et al., 1997, Proc. Natl. Acad. Sci. USA 94:2095–2097.
Hayn, et al., 1996, Life Sci. 59:537–544.
Hensley, et al., 1994, Proc. Natl. Acad. Sci USA 91:3270–3274.
Hwang, et al., 1994, J. Am. Chem. Soc. 116:10829–10830.
Kanai, et al., 1998, Ann Neurol. 44:17–26.
Lawson, et al., 1999, J. Biol Chem., 274:24441–24444.
Lawson, et al., 1998, J. Biol Chem. 273:29295–29301.
Li, et al., 1999, PNAS 96:13381–13386.
Lovell, et al., 1997, Neurobiol. Aging 18:457–461.
Lovell, et al., 1995, Neurology 45:1594–1601.
Lyras, et al., 1997, J. Neurochem. 68:2061–2069.
Mahley, et al., 1995, Curr. Opin. Lipidol. 6:86–91.
Mattson, et al., 1992, Neurosc. 12:376–389.
Mayeux, et al., 1993, Ann. Neurol. 34:752–754.
Meagher, et al., 1999, J. Clin. Invest. 104:805–813.
Montine et al, 1998, Ann. Neurol. 44:410–413.
Montine, et al., 1997, J. Neuropath. Exper. Neurol. 56:866–871.
Morrow, et al., 1994, J. Biol. Chem. 269:4317–4326.
Morrow, et al., 1996, Biochem, Pharmacol. 51:1–9.
Morrow, et al., 1997, Prog. Lipid Res. 36:1–22.
Nakamura, et al., 1994, Ann. Neurol 36:903–911.
Palmer, et al., 1994, Brain Res. 645:338–342.

(List continued on next page.)

*Primary Examiner*—Ralph Gitomer
(74) *Attorney, Agent, or Firm*—Morgan Lewis & Bockius, LLP

(57) ABSTRACT

The invention includes methods useful for the diagnosis of Alzheimer's disease and the evaluation of enhanced levels of lipid peroxidation in a mammal. The methods utilize isoprostanes as sensitive and stable molecular markers for lipid peroxidation in a mammal. Methods of identifying compounds useful for the treatment of Alzheimer's disease or for reducing levels of lipid peroxidation in a mammal are also included. The invention also includes kits useful for the diagnosis of Alzheimer's disease and for the evaluation of levels of lipid peroxidation in a mammal.

32 Claims, 7 Drawing Sheets

OTHER PUBLICATIONS

Patrona, et al., 1997, Arterioscl. Thromb Vasc. Biol. 17:2309–2315.
Petersen, et al., 1995, JAMA 273:1274–1278.
Pratico, et al., 1995, J. Biol. Chem 270:9800–9808.
Pratico, et al., 1996, J. Biol Chem. 271:8919–8924.
Pratico, et al., 1997, J. Clin. Inv. 100:2028–2034.
Practico, et al., 1998, Nature Med. 4:1189–1192.
Practico, et al., 1999, Atheroscler, 147:1–10.
Pratico, et al., 1999, J. Neurochem. 73:736–741.
Pudukulathan, et al., 1998, J. Am. Chem. Soc. 120:11953–11961.
Reilly, et al., 1996, Circulation 94:19–25.
Reilly, et al., 1996, Circulation 94:3727 (A).
Reilly, et al., 1997, Circulation 96:3314–3320.
Rokach, et al., 1997, Prostaglandins 54:853–873.
Sayre, et al., 1997, J. Neurochem. 68:2092–2097.
Scheuner, et al., 1996, Nature Med. 2:864–870.
Schmidt, et al., 1991, Lab. Invest. 64:352–357.
Schmidt, et al., 1996, Acta Neuropathol. 91:475–481.
Selkoe, et al., 1997, Science 275:630–631.
Subbarao, et al., 1990, J. Neurochem. 55:342–345.
Takahashi, et al., 1992, J. clin. Invest. 90:136–141.
Tato, et al., 1995, J. Neurol. Neurosurg. Psychiatry 59:280–283.
Thomas, et al., 1996, Nature 380:168–171.
Turner, et al., 1996, J. Biol. Chem. 271:8966–8970.
Van Duijn, et al., 1996, J. Neurol Neurosug. Psychiatry 60:478–488.
Van Duijn, et al., 1994, Nature Genet. 7:74–78.
Wenham, et al., 1991, Lancet 337:1158–1159.
Adiyaman et al., 1998, Anal. Biochem. vol. 262, No. 1, pp. 45–56.
Practico et al., 1998, Proc. Acad. Sci., USA, vol. 95, No. 7, pp. 3449–3454.
Practico et al., 1998, FASEB Journal, vol. 12, No. 15, pp. 1777–1783.

* cited by examiner iPF$_{2\alpha}$-III (8-iso-PGF$_{2\alpha}$)

iPF$_{2\alpha}$-VI

8,-12-iso-iPF$_{2\alpha}$-VI

METHODS AND COMPOSITIONS FOR DETERMINING LIPID PEROXIDATION LEVELS IN OXIDANT STRESS SYNDROMES AND DISEASES

CROSS-REFERENCE TO RELATED APPLICATIONS

This application is a continuation of PCT/US99/28583 filed Dec. 2, 1999 and further, this application is entitled to priority pursuant to 35 U.S.C. §119(e) to U.S. Provisional Patent Application No. 60/110,569, which was filed on Dec. 2, 1998.

STATEMENT REGARDING FEDERALLY SUPPORTED RESEARCH AND DEVELOPMENT

This invention was supported in part by U.S. Government funds (NIH Grant Nos. HL 5400, AG-09215 and AG-10124), and the U.S. Government may therefore have certain rights in the invention.

BACKGROUND OF THE INVENTION

Alzheimer's Disease (AD) is a neurodegenerative disorder characterized by a progressive decline in cognitive function, as well as by numerous amyloid plaques, neurofibrillary tangles (NFTs) and extensive neuronal loss in the brains of AD patients (Morrison-Bogorad et al., 1997, In *The Molecular and Genetic Basis of Neurological Disease*, Second edition, Butterworth-Heinemann, eds., pp 581–600). Although epidemiolgic studies have failed to identify a single cause of AD, genetic studies have implicated several mutations in three separate genes on different chromosomes that encode the amyloid-(A) precursor proteins (APP), presenilin-1 (PS-1), and presenilin-2 (PS-2) as the cause of autosomal dominantly inherited AD in a subset of kindreds with familial AD (FAD) (Van Duijn, 1996, J. Neurol. Neurosurg. Psychiatry 60:478–488; Goedert et al., 1997, In: *The Molecular and Genetic Basis of Neurological Disease*, Second edition, Butterworth-Heinemann, eds. pp. 613–628; Selkoe, 1997, Science 275:630–631). In addition, the 4 allele of the apolipoprotein E (APOE) gene has been shown to be a genetic risk factor for AD (Selkoe, 1997, Science 275:630–631). However, all of the known FAD mutations account for less than 5% of affected patients, since the majority of AD cases are sporadic and there is only modest evidence in support of familial clustering (Hardy, 1997, Proc. Natl. Acad. Sci USA 94:2095–2097).

Despite this heterogeneity, common factors may be involved in the pathogenesis of both hereditary and sporadic AD. These factors may promote the formation of A deposits and NFTs, as well as the massive degeneration of neurons in selected regions of all AD brains (Morrison-Bogorad et al., 1997 In: *The Molecular and Genetic Basis of Neurological Disease*, Second edition, Butterworth-Heinemann, eds. pp. 581–600). It has been suggested that the abnormal processing or production of A and plaque formation are pivotal events in the pathogenesis of the disease (Scheuner et al., 1996, Nature Med. 2:864–870; Mattson et al., 1992, Neurosc. 12:376–389). Furthermore, aggregated, but not monomeric species of A are hypothesized to induce the dysfunction and death of neurons in vitro by a range of mechanisms (Busciglio et al., 1995, Neuron. 14:879–888; Thomas et al., 1996, Nature 380:168–171; Behl et al., 1994, Cell 77:817–827). It has been hypothesized that AD brain regions which have accumulations of numerous A-rich senile plaques (SPs) are loci of elevated oxidative stress, perhaps reflective of an inflammatory reaction (Hensley et al, 1994, Proc. Natl. Acad. Sci. USA 91:3270–3274). Furthermore, it has been suggested that oxidant stress may be of functional importance in the pathogenesis of AD and that the production of reactive oxygen species (ROS) in the brain leads to lipid peroxidation and neuronal degeneration in AD (Gotz et al., 1994, Proc. Natl. Acad. Sci. USA 91:3270–3274).

Although there has been much speculation that ROS may play an important role in AD, there have been few data in support of this hypothesis. Efforts to elucidate the role of lipid peroxidation and oxidant stress in vivo have been hampered by the paucity of reliable quantitative molecular markers. Currently available molecular markers have been of limited value due to their chemical instability or their lack of sensitivity or specificity (Gutteridge and Halliwell, 1990, Trends Biochem. Sci. 15:129–1365).

The few studies which have been reported thus far of lipid peroxidation in the AD brain have provided evidence for increased lipid peroxidation by measuring levels of thiobarbituric acid reactive substances (TBARS) (Subbarao et al., 1990, J. Neurochem. 55:342–345; Palmer and Burns, 1994, Brain Res. 645:338–342; Lovell et al., 1995, Neurology 45:1594–1601; Balazs and Leon, 1994, Neuroch. Res. 19:1131–1137). However, the validity of this method is limited because it measures other aldehydes conjugated to TBARS, as well as non-lipid related chromogens. Recently, two separate groups of investigators have reported no difference in the level of TBARS and lipid hydroperoxides in AD versus control brains (Lyras et al., 1997, J. Neurochem. 68:2061–2069; Hayn et al., 1996, Life Sci. 59:537–544). Immunohistochemical data suggest the presence in AD brain of stable by-products of lipid peroxidation (Montine et al., 1997, J. Neuropath. Exper. Neurol. 56:866–871; Sayre et al., 1997, J. Neurochem. 68:2092–2097). While increased levels of 4-hydroxynonenal in post-mortem CSF of AD patient has been reported, no such quantitative data are available for this compound in AD brains (Lovell et al., 1997, Neurobiol. Aging 18:457–461).

Thus, there is an unmet need in the art for compositions and methods relating to molecular markers of oxidant stress or lipid peroxidation in a mammal for use in the diagnosis, treatment and development of therapeutics for diseases which manifest oxidant stress, such as Alzheimer's disease. The present invention meets these needs.

BRIEF SUMMARY OF THE INVENTION

The invention relates to a method of measuring the level of lipid peroxidation in a mammal suspected of having an oxidant stress syndrome or disease. The method comprises a) obtaining a first sample of a tissue or body fluid from the mammal; b) assessing the level of an isoprostane molecular marker for lipid peroxidation present in the first sample; and, c) comparing the level of the isoprostane molecular marker present in the first sample with the level of the isoprostane molecular marker present in a second sample of a tissue or body fluid obtained from an otherwise identical mammal which is not afflicted with an oxidant stress syndrome or disease, wherein an elevated level of the isoprostane molecular marker in the first sample relative to the level of the isoprostane molecular marker in the second sample, is indicative of an elevated level of lipid peroxidation in the mammal, thereby indicating the presence of an oxidant stress syndrome or disease in the mammal.

In one aspect, the method further comprises after a) and prior to b) isolating from the first sample the isoprostane molecular marker.

In another aspect, the elevated level of lipid peroxidation comprises an elevated level of a reactive oxygen species (ROS).

In yet another aspect, the elevated level of lipid peroxidation comprises an elevated level of inflammation.

In one embodiment, the elevated level of inflammation comprises elevated cyclooxygenase (COX) activity.

In yet a further aspect, the oxidant stress disease is Alzheimer's disease.

In another aspect, the isoprostane molecular marker is selected from the group consisting of $iPF_{2\alpha}$-III, $iPF_{2\alpha}$-VI and 8,12-iso-$iPF_{2\alpha}$-VI.

In an additional aspect, the tissue is brain tissue.

In one embodiment, the brain tissue is selected from the group consisting of brain frontal pole tissue and brain temporal pole tissue.

In another embodiment, the body fluid is selected from the group consisting of cerebrospinal fluid (CSF), plasma and urine.

The invention also relates to a method of diagnosing an oxidant stress syndrome or disease in a mammal. The method comprises a) obtaining a first sample of a tissue or body fluid from the mammal; b) assessing the level of the isoprostane molecular marker present in the first sample; and, c) comparing the level of the isoprostane molecular marker present in the first sample with the level of the isoprostane molecular marker present in a second sample of a tissue or body fluid obtained from an otherwise identical mammal which is not afflicted with the oxidant stress syndrome or disease, wherein an elevated level of the isoprostane molecular marker in the first sample relative to the level of the isoprostane molecular marker in the second sample, is indicative of an elevated level of lipid peroxidation in the mammal, whereby the oxidant stress syndrome or disease is diagnosed in the mammal.

In one aspect, the method further comprises after a) and before b) isolating from the first sample the isoprostane molecular marker.

Also included in the invention is a method of measuring the level of an isoprostane molecular marker for lipid peroxidation in a mammal suspected of having an oxidant stress syndrome or disease. The method comprises a) obtaining a sample of a tissue or body fluid from the mammal; b) isolating from the sample the isoprostane molecular marker by using a total lipids solvent extraction method; c) assaying the isoprostane molecular marker from b); and, d) quantifying the level of the isoprostane molecular marker.

In one aspect, the assaying comprises using a gas chromatography/mass spectrometry assay method which comprises a synthetic homologous isoprostane standard, and further wherein the quantifying is performed using peak area or peak height ratios.

In another aspect, the oxidant stress disease is Alzheimer's disease. In yet another aspect, the isoprostane molecular marker is selected from the group consisting of $iPF_{2\alpha}$-III, $iPF_{2\alpha}$-VI and 8,12-iso-$iPF_{2\alpha}$-VI.

In an additional aspect, the tissue is brain tissue.

In one embodiment, the brain tissue is selected from the group consisting of brain frontal pole tissue and brain temporal pole tissue.

In another aspect, the body fluid is selected from the group consisting of cerebrospinal fluid (CSF), plasma and urine.

The invention further relates to a method of identifying a compound useful for the treatment of Alzheimer's disease in a mammal. The method comprises a) measuring the level of an isoprostane molecular marker for lipid peroxidation in either a sample of a tissue or body fluid obtained from a first mammal prior to administering the compound, or, in a sample of a tissue or body fluid obtained from an otherwise identical second mammal which is not to be administered the compound; b) administering the compound to the first mammal; c) thereafter measuring the level of the isoprostane molecular marker in a tissue or body fluid obtained from the first mammal; and, d) comparing the level of the isoprostane molecular marker measured in c) with the level of the isoprostane molecular marker measured in a), wherein when the level of the isoprostane molecular marker measured in c) is reduced relative to the level of the isoprostane molecular marker measured in a), a compound useful for the treatment of Alzheimer's disease in a mammal is identified.

In one aspect, the isoprostane molecular marker of lipid peroxidation is selected from the group consisting of $iPF_{2\alpha}$-III, $iPF_{2\alpha}$-VI and 8,12-iso-$iPF_{2\alpha}$-VI.

In another aspect, the tissue is brain tissue selected from the group consisting of brain frontal pole tissue and brain temporal pole tissue.

In another aspect, the body fluid is selected from the group consisting of cerebrospinal fluid (CSF), plasma and urine.

The invention also relates to a method of identifying an effective amount of a compound useful for the treatment of Alzheimer's disease in a mammal. The method comprises a) measuring the level of an isoprostane molecular marker for lipid peroxidation in either a sample of a tissue or body fluid obtained from a first mammal prior to administering the compound, or, in a sample of a tissue or body fluid obtained from an otherwise identical second mammal which is not to be administered the compound; b) administering to the first mammal an amount of the compound; c) thereafter measuring the level of the isoprostane molecular marker in a tissue or body fluid obtained from the first mammal; and, d) comparing the level of the isoprostane molecular marker measured in c) with the level of the isoprostane molecular marker measured in a), wherein when the level of the isoprostane molecular marker measured in c) is reduced relative to the level of the isoprostane molecular marker measured in a), an effective amount of a compound useful for the treatment of Alzheimer's disease in a mammal is identified.

The invention also includes a method of determining the optimal concentration of a compound useful for the treatment of Alzheimer's disease. The method comprises monitoring the level of an isoprostane molecular marker for lipid peroxidation in a series of mammals administered the compound at a series of concentrations of compound, wherein the concentration of the compound which results in maximal reduction of the level of the isoprostane molecular marker in one or more of the series of mammals, which concentration is not toxic to the mammals, is the optimal concentration.

Also included is a method of determining the optimal dosage frequency of a compound useful for the treatment of Alzheimer's disease. The method comprising monitoring the level of an isoprostane molecular marker for lipid peroxidation in a series of mammals administered the compound at a series of dosage frequencies, wherein the dosage frequency of the compound which results in maximal reduction of the level of the isoprostane molecular marker in one or more of the series of mammals, which dosage is not toxic to the mammals, is the optimal dosage frequency.

In one aspect, the compound is an antioxidant compound.

In another aspect, the compound is an anti-inflammatory compound, wherein the compound is administered at a series of concentrations effective to inhibit the activity of a cyclooxygenase (COX) enzyme in a mammal.

The invention further relates to a method of identifying a compound useful for reducing the level of an isoprostane molecular marker for lipid peroxidation in a sample of a tissue or body fluid obtained from a first mammal. The method comprises a) measuring the level of the isoprostane molecular marker in either a sample of a tissue or body fluid obtained from the first mammal prior to administering the compound, or, in a sample of a tissue or body fluid obtained from an otherwise identical second mammal which is not to be administered the compound; b) administering the compound to the first mammal; c) thereafter measuring the level of the isoprostane molecular marker in a tissue or body fluid sample obtained from the first mammal; d) comparing the level of the isoprostane molecular marker measured in c) with the level of the isoprostane molecular marker measured in a), wherein when the level of the isoprostane molecular marker measured in c) is reduced relative to the level of the isoprostane molecular marker measured in a), a compound useful for reducing the level of an isoprostane molecular marker in a mammal is identified.

In one aspect, the compound is present in an amount effective to inhibit the activity of a cyclooxygenase enzyme in the brain tissue of the mammal.

In another aspect, the compound is present in an amount effective to reduce the level of a reactive oxygen species in the brain tissue of the mammal.

In yet another aspect, the isoprostane molecular marker of lipid peroxidation is selected from the group consisting Of $iPF_{2\alpha}$-III, $iPF_{2\alpha}$-VI and 8,12-iso-$iPF_{2\alpha}$-VI.

Also included is a kit for diagnosing Alzheimer's disease in a mammal. The kit comprises a) a sample container for carrying a tissue or body fluid sample from the mammal; b) a solution for use in extraction of an isoprostane molecular marker for lipid peroxidation from the tissue or body fluid sample obtained from the mammal; c) a negative control solution of the isoprostane molecular marker of lipid peroxidation present at a concentration of about the concentration of the isoprostane molecular marker present in a tissue or body fluid sample of a mammal which is not afflicted with Alzheimer's disease; d) a positive control solution of the isoprostane molecular marker of lipid peroxidation present at a concentration of about the concentration of the isoprostane molecular marker in a tissue or body fluid sample of a mammal which is afflicted with Alzheimer's disease; e) an antibody directed against an isoprostane molecular marker for lipid peroxidation; and, f) an instructional material.

Further included is a kit for measuring the level of an isoprostane molecular marker for lipid peroxidation in a tissue or body fluid sample obtained from a mammal. The kit comprises a) a sample container for carrying a tissue or body fluid sample from the mammal; b) a solution for use in extraction of an isoprostane molecular marker of lipid peroxidation from the tissue or body fluid sample obtained from the mammal; c) a negative control solution of the isoprostane molecular marker of lipid peroxidation present at a concentration of about the concentration of the isoprostane molecular marker present in a tissue or body fluid sample of a mammal which is not afflicted with Alzheimer's disease; d) a positive control solution of the isoprostane molecular marker of lipid peroxidation present at a concentration of about the concentration of the isoprostane molecular marker in a tissue or body fluid sample of a mammal which is afflicted with Alzheimer's disease; e) an antibody directed against an isoprostane molecular marker for lipid peroxidation; and, f) an instructional material.

BRIEF DESCRIPTION OF THE DRAWINGS

The foregoing summary, as well as the following detailed description of the invention, will be better understood when read in conjunction with the appended drawings.

FIG. 7, comprising

DETAILED DESCRIPTION OF THE INVENTION

Figure 1:
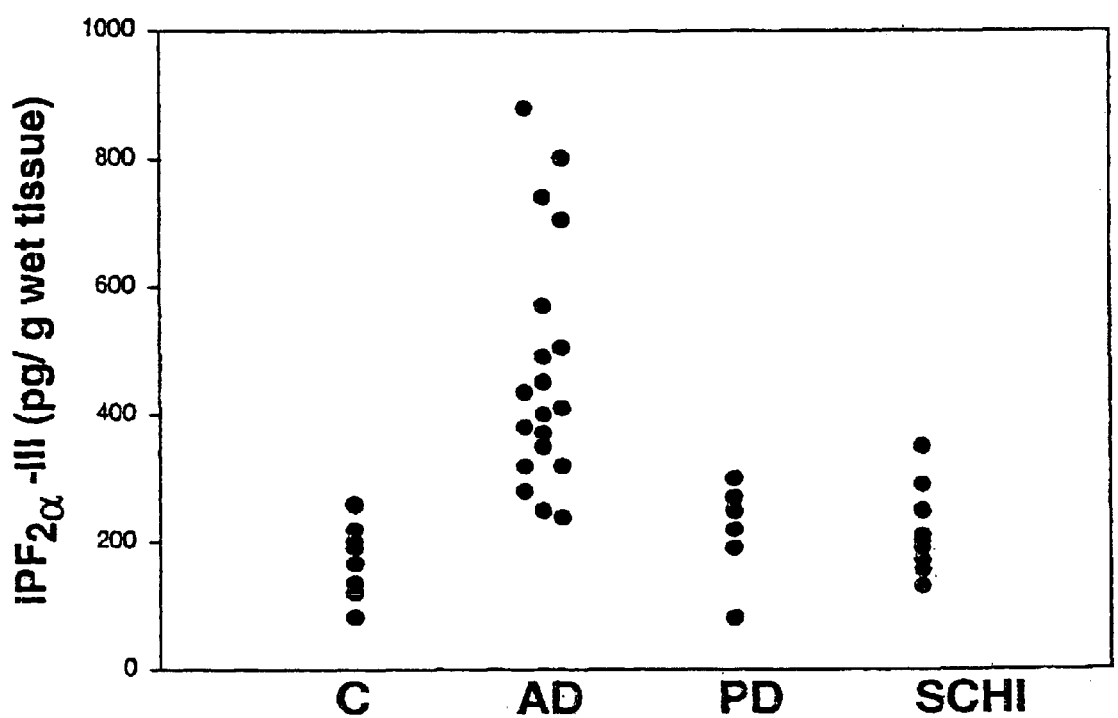
FIG. 1 is a graph depicting levels of the isoprostane $iPF_{2\alpha}$-III in tissue samples obtained from the brain frontal pole of normal controls (C), Alzheimer's disease (AD), Parkinson's disease (PD) and Schizophrenia (SCHI) patients. The levels of $iPF_{2\alpha}$-III are expressed in picograms per gram of wet tissue sample.

The present invention relates to compositions and methods useful in the assessment of the level of lipid peroxidation in a mammal. An enhanced level of lipid peroxidation in a mammal is a useful indication of the presence of an oxidant stress syndrome or disease, such as Alzheimer's disease. Such an enhanced level of lipid peroxidation may result from any one of several factors, including, by way of example and not by limitation, an elevated level of a reactive oxygen species (ROS), an elevated level of inflammation, and an elevated level of oxidant stress.

The methods and compositions of the invention employ a class of molecules termed isoprostanes as molecular markers of lipid peroxidation. Isoprostanes (iP) are prostaglandin (PG) isomers that are produced by free radical attack on arachidonic acid in situ in membrane phospholipids (Morrow et al., 1992, J. Biol. Chem. 268:4161–4169). They offer advantages over conventional indices of lipid peroxidation.

For example, in contrast to lipid hydroperoxides, which rapidly decompose, isoprostanes are chemically stable end-products of lipid peroxidation, that are released by phospholipases, circulate in plasma and are excreted in urine (Awad et al., 1993, J. Biol. Chem. 268:4161–4169). While isomers of prostaglandins, leukotrienes and epoxyeicosatrienoic acids may be formed in this manner, attention has been focused on isomers of $PGF_2$, the $F_2$-isoprostanes ($F_2$-iPs).

The present invention relates to specific and sensitive methods for measuring three distinct $F_2$-isoprostanes, 8-iso-$PGF_2$ (now known as $iPF_2$-III), $iPF_2$-I (now known as $iPF_2$-VI) and 8,12-iso-$iPF_2$-VI as molecular markers of lipid peroxidation in vitro and in vivo (Pratico et al., 1995, J. Biol. Chem. 270:9800–9808; Pratico et al., 1998, Proc. Natl. Acad. Sci. USA 95:3449–3454; Rokach et al, 1997, Prostaglandins 54:853–873; Pratico et al., 1996, J. Biol. Chem. 271:8919–8924; Reilly et al., 1996, Circulation 94:19–25; Delanty et al., 1997, Circulation 95:2492–2499). Given the mechanism of their formation and clearance, isoprostanes reflect lipid peroxidation at the tissue site of free radical generation or in body fluids such as, for example, cerebrospinal fluid (CSF). $IPF_2$-III has previously been reported to be elevated in human atherosclerosis plaques, wherein the isoprostane is found localized to monocyte/macrophages and smooth muscle cells, and in circulating low density lipoprotein as well as in the urine from hypercholesterolemic subjects (Pratico et al., 1997, J. Clin. Inv. 100:2027–2034; Reilly et al., 1996, Circulation 94:3727(A)).

The formation of isoprostanes, which are stable compounds in vivo, can be reliably monitored through non-invasive analytical approaches. Thus, these molecules are useful as sensitive and specific molecular markers of the level of lipid peroxidation in a mammal (Patrona and FitzGerald, 1997, Arteriosc. Thromb. Vasc. Biol. 17:2309–2315; Morrow and Roberts, 1996, Biochem, Pharmacol. 51:1–9). For these reasons, the present invention includes specific and sensitive methods for measuring the level of isoprostanes, exemplified by three specific $F_2$-isoprostanes, $iPF_2$-III, $iPF_2$-VI and 8,12-iso-$iPF_2$-VI. It has been previously reported that $iPF_2$-III generation is elevated in several syndromes putatively associated with oxidant stress in vivo, including cigarette smoking and coronary reperfusion (Pratico and FitzGerald, 1996, J. Biol. Chem. 271:8919–8924; Reilly et al., 1996, Circulation 94:19–25; Reilly et al., 1997, Circulation 96:3314–3320). $F_2$-isoprostanes are elevated in situ, at the site of their formation in human atherosclerotic plaques, where lipid peroxidation is thought to occur in vivo (Pratico et al., 1997, J. Clin. Inv. 100:2027–2034). However, until the present invention, it has not been shown that these three specific isoprostanes can be used in methods and compositions useful in the diagnosis, treatment, and development of therapeutics for neurodegenerative diseases such as Alzheimer's disease.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, the term "isoprostane" means a free radical-catalyzed prostaglandin isomer formed from arachidonic acid. An isoprostane is an isomer of a prostaglandin.

As used herein, the term "oxidant stress" means the consequences of free radical dependent damage to proteins, DNA and/or lipid without regard to the specific radical involved or the relative preponderance of the targets. "Oxidant stress" implies radical generation in excess of that which can be quenched (i.e., coped with) by the endogenous antioxidant defenses of a mammal, and implies tissue or organ dysfunction in the mammal, and is thus a potential mechanism of disease.

As used herein, the term "oxidant stress syndrome or disease" means any disease or syndrome either caused by oxidant stress or of which oxidant stress is a symptom. For example, a neurodegenerative oxidant stress disease is a neurodegenerative disease which is either caused by oxidant stress, or of which oxidant stress is a symptom.

As used herein, the term "lipid peroxidation" means the consequence of free radical damage to lipids.

As used herein, the term "isoprostane molecular marker for lipid peroxidation" means a derivative of the process of lipid peroxidation which reflects the occurrence of the process in a quantitative manner.

As used herein, the term "treatment of Alzheimer's disease" means an intervention of a pharmacological or nutritional nature of which the objective is any one or more of the following: arresting or retarding the progress of Alzheimer's disease, inducing its regression, diminishing the likelihood of its occurrence or recurrence, or alleviating any one or more of its symptoms.

As used herein, the term "substantially purified" or "substantially pure" means a compound, e.g., a protein or a lipid which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of proteins by column chromatography, gel electrophoresis or HPLC analysis. A compound, e.g., a protein, is also substantially purified when it is essentially free of naturally associated components or when it is separated from the native contaminants which accompany it in its natural state. Included within the meaning of the term "substantially pure" as used herein is a compound, such as a protein or lipid, which is homogeneously pure, for example, where at least 95% of the total protein (by volume, by wet or dry weight, or by mole percent or mole fraction) in a sample is the protein or lipid of interest.

Description

In all of the methods and compositions of the invention described herein, the mammal can be any mammal, and is preferably a human. The methods of the invention can be performed either on a mammal which manifests a symptom or symptoms of an oxidant stress syndrome or disease, or on a mammal which does not manifest a symptom or symptoms of an oxidant stress syndrome or disease. Furthermore, the methods of the invention may be performed on the mammal at any stage in the progression of an oxidant stress syndrome or disease. Additionally, the methods of the invention may be performed on a mammal suspected of being predisposed to an oxidant stress syndrome or disease for reasons such as environmental factors and genetic factors.

In all of the methods and compositions of the invention described herein, the oxidant stress syndrome or disease is a neurodegenerative syndrome or disease such as, for example, Alzheimer's disease, Amyotropic Lateral Sclerosis, Down's syndrome, and Parkinson's disease (localized to the substantia nigra). Preferably, the disease is Alzheimer's disease.

Also, in the methods and compositions of the invention described herein, the tissue sample can be a tissue sample obtained from any type of tissue, and the body fluid sample can be obtained from any type of body fluid.

In the methods of the invention where a first sample from a first mammal is compared to a second sample obtained from an otherwise identical second mammal, the second sample is preferably obtained from the same tissue type or body fluid type as the first sample. Preferably, the tissue sample is obtained from brain tissue. Preferably the body fluid sample is a sample obtained from the group consisting of cerebrospinal fluid (CSF), plasma and urine. CSF samples of about 100 microliters or greater, plasma samples of about 2 milliliters or greater, and urine samples of about 5 milliliters or greater are preferred amounts of samples.

The methods of the invention can be performed as non-invasive methods, which may be used, for example, on an out-patient, or clinical setting basis. These embodiments are useful in convenient screening procedures for patients suspected of having a oxidant stress syndrome or disease.

The methods of the invention can also be performed as invasive methods, which require, for example, a biopsy sample, or a sample obtained during a surgical procedure. Also, the invasive methods may be used as part of an autopsy procedure. In these embodiments, the sample of a tissue is preferably a sample of brain tissue. Preferably, the brain tissue is a brain tissue selected from the group consisting of brain frontal pole tissue and brain temporal pole tissue. Brain tissue samples having a mass of about a few grams or greater are used in the methods of the invention. Examples of body fluid samples in these invasive embodiments include, among others, pericardial fluid, gall bladder fluid, and other body fluids at sites of local oxidant stress.

Furthermore, in all of the methods and compositions of the invention, the isoprostane molecular marker for lipid peroxidation is preferably an isoprostane selected from the group consisting of $iPF_{2\alpha}$-III, $iPF_{2\alpha}$-VI and 8,12-iso-$iPF_2$-VI.

Any of the methods of the invention can, optionally, include after obtaining a sample of tissue or body fluid from the mammal, isolating from the sample an isoprostane molecular marker for lipid peroxidation. Preferably, the isoprostane molecular marker is an isoprostane selected from the group consisting of $iPF_{2\alpha}$-III, $iPF_2$-VI and 8,12-iso-$iPF_2$-VI. The isoprostane molecular marker can be isolated from the sample by any method known to the skilled artisan for isolating a prostaglandin molecule (See, for example, Pratico et al., 1995, J. Biol. Chem. 270:9800–9808 and Pratico et al., 1998, Proc. Natl. Acad. Sci. USA 95:3449–3454).

Such methods include, by way of example, and not by limitation, purification methods such as solvent extractions, solid phase extractions, chromatographic methods, thin-layer chromatography methods, centrifugation and sedimentation methods, among others. An example of an isolation method is described herein in the Examples.

Furthermore, the methods of the invention can, optionally, include isolating a substantially pure isoprostane molecular marker using any of the methods and techniques known to the skilled artisan or described herein for isolating a prostaglandin molecule.

All of the methods of the invention also include either assessing the level of, measuring, assaying or quantifying the level of an isoprostane molecular marker for lipid peroxidation in a tissue or body fluid sample obtained from a mammal. Techniques and methods for assessing, measuring, asssaying or quantifying a prostaglandin molecule are known to the skilled artisan. Such methods include, for example, methods for assessing or quantifying the level of prostaglandins. Such methods are described, for example, in Lawson et al. (1999, J. Biol. Chem., 374(35) 24441–24444). These methods include, by way of example, and not by limitation, quantitative and semi-quantitative methods such as chromatographic methods including thin layer chromatography, low, medium, and high pressure liquid chromatography methods, mass spectrometry methods, gas chromatography methods, gas chromatography/mass spectrometry methods, and immunological methods. An example of assessing the level of an isoprostane molecular marker in a tissue or body fluid sample is described herein in the Examples.

The invention also encompasses the use of pharmaceutical compositions of an appropriate compound to practice the methods of the invention, the compositions comprising an appropriate compound and a pharmaceutically-acceptable carrier. The compound may be, by way of example and not by limitation, an antioxidant compound or an anti-inflammatory compound.

As used herein, the term "pharmaceutically-acceptable carrier" means a chemical composition with which an appropriate compound may be combined and which, following the combination, can be used to administer the appropriate compound to a mammal.

The pharmaceutical compositions useful for practicing the invention may be administered to deliver a dose of from about 1 nanogram per kilogram of body weight per day and about 100 grams per kilogram of body weight per day.

Pharmaceutical compositions that are useful in the methods of the invention may be administered systemically in oral solid formulations, ophthalmic, suppository, aerosol, topical or other similar formulations. In addition to the appropriate compound, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate compound according to the methods of the invention.

The invention includes a method of measuring the level of lipid peroxidation in a mammal suspected of having an oxidant stress syndrome or disease.

The method comprises obtaining a first sample of a tissue or body fluid from the mammal, assessing the level of an isoprostane molecular marker for lipid peroxidation present in the first sample, and comparing the level of the isoprostane molecular marker present in the first sample with the level of the isoprostane molecular marker in a second sample of a tissue or body fluid obtained from an otherwise identical mammal which is not afflicted with the oxidant stress syndrome or disease. The second sample of a tissue or body fluid can be obtained from the same or a different type of tissue or body fluid as the first sample.

In preferred embodiments, the second sample is of the same tissue type or body fluid type as in the first sample. Preferably, the first and second sample of body fluid are cerebrospinal fluid. Also, in another preferred embodiment, the first and second sample of a tissue are both brain tissue. Preferably, the brain tissue is a tissue selected from the group consisting of brain frontal pole tissue and brain temporal pole tissue.

In another embodiment, the second sample of a tissue or body fluid is a sample of a tissue or body fluid obtained from a mammal, wherein the tissue or body fluid is not typically affected by an oxidant stress syndrome or disease. For example, in the case of Alzheimer's disease, the second sample of a tissue may be a sample of brain cerebellum tissue, since the cerebellum is typically not affected by Alzheimer's disease.

The level of the isoprostane molecular marker present in the second sample is preferably assessed by the same method used in assessing the level of the isoprostane molecular marker in the first sample. In comparing the level of the isoprostane molecular marker in the first sample with the level in the second sample, an elevated level of the isoprostane molecular marker in the first sample relative to the level of the isoprostane molecular marker in the second sample is indicative of an elevated level of lipid peroxidation in the mammal. This is taken as an indication of the presence of oxidant stress syndrome or disease in the mammal. Preferably, the elevated level is a level that is at least about 20% greater than the level of the isoprostane molecular marker in the second sample.

The elevated level of lipid peroxidation which is detected by the method of the invention may arise from the presence of any one or more of several factors. In one embodiment, the elevated level of lipid peroxidation arises from the presence of an elevated level of a reactive oxygen species in a tissue or body fluid of the mammal.

In another embodiment, the elevated level of lipid peroxidation arises from the presence of an elevated level of inflammation in a tissue or body fluid of the mammal. Preferably, the elevated level of inflammation is the result of an elevated level of a cyclooxygenase (COX) enzyme activity.

The invention also includes a method of diagnosing an oxidant stress syndrome or disease in a mammal. The method comprises measuring the level of lipid peroxidation in the mammal. An elevated level of lipid peroxidation in the mammal is indicative of the presence of an oxidant stress syndrome or disease, since a symptom of an oxidant stress syndrome or disease is the presence of an elevated level of a ROS in a tissue or body fluid of the mammal, and this elevated level of a ROS causes an increase in the level of lipid peroxidation in the tissue or body fluid of the mammal.

In this method, a first sample of a tissue or body fluid is obtained from the mammal. The level of an isoprostane molecular marker present in the first sample is then assessed by any of the methods or techniques described herein or known to the skilled artisan. The level of the isoprostane molecular marker present in the first sample is then compared with the level of the isoprostane molecular marker present in a second sample of a tissue or body fluid obtained from an otherwise identical mammal which is not afflicted with the oxidant stress syndrome or disease being diagnosed.

Preferably, the second sample of a tissue or body fluid is obtained from an otherwise identical mammal which is not afflicted with any oxidant stress syndrome or disease. The level of the isoprostane molecular marker present in the second sample of a tissue or body fluid is preferably assessed by the same method used in assessing the level of the isoprostane molecular marker in the first sample.

In comparing the levels, an elevated level of the isoprostane molecular marker in the first sample relative to the level of the isoprostane molecular marker in the second sample is indicative of an elevated level of lipid peroxidation in the mammal. This is taken as a positive diagnosis for the presence of the oxidant stress syndrome or disease in the mammal. An elevated level is a level which is at least about 20% greater than the level of the isoprostane molecular marker present in the second sample of tissue or body fluid. The second sample of a tissue or body fluid serves as the negative control. In one embodiment, the second sample is obtained from an otherwise identical mammal which is afflicted with the oxidant stress syndrome being diagnosed, but the sample is obtained from a tissue or body fluid which is typically not affected by the disease. For example, the tissue type of the second tissue sample may be a sample of brain cerebellum tissue when the oxidant stress disease being diagnosed is Alzheimer's disease, since the cerebellum is normally not affected by the disease.

The invention further includes a method of measuring the level of an isoprostane molecular marker for lipid peroxidation in a mammal suspected of having an oxidant stress syndrome or disease. The method comprises obtaining a sample of a tissue or body fluid from the mammal. An isoprostane molecular marker is then isolated from the sample. The isoprostane molecular marker can be isolated by any method described herein or known by the skilled artisan. A preferred method of isolating the isoprostane molecular marker is described herein in the Examples. Briefly, the isoprostane molecular marker is isolated by first, in the case of a tissue sample, homogenizing the tissue sample. In the case of a body fluid sample, no homogenization step is necessary. Total lipids are then extracted from the sample using ice-cold Folch solution, cloroform/methanol (2:1,v/v). The solution is then centrifuged briefly, and the organic phase, which contains the extracted lipids, is dried under nitrogen. Lipids are then hydrolyzed using aqueous potassium hydroxide to release the isoprostane molecular marker.

The isoprostane molecular marker isolated as described above is then assayed using an assay method for an isoprostane. Preferably, the assay is a quantitative assay. The level of the isoprostane molecular marker is then quantified based on the assay results using, for example, peak area or peak height ratios. An example of a preferred quantitative assay for an isoprostane is described herein in the Examples (See, also Pratico et al., 1998, Proc. Natl. Acad. Sci. USA 95:3449–3454).

For example, the isoprostane molecular marker isolated as described above can be assayed as follows. Briefly, after potassium hydroxide hydrolysis, the sample which contains an isoprostane is spiked with a known amount of a synthetic homologous internal standard, which can be, for example, a radio-labeled synthetic homologous isoprostane molecule. The samples are then subjected to solid phase extraction, derivatized, and purified using thin layer chromatography. After thin layer chromatography, each sample is analyzed for isoprostane content using gas chromatography-mass spectrometry, and quantitation is performed using peak area or peak height ratios.

The invention also includes a method of identifying a compound useful for the treatment of Alzheimer's disease in a mammal. The method comprises measuring the level of an isoprostane molecular marker for lipid peroxidation in either a sample of a tissue or body fluid obtained from a first mammal prior to administering the compound, or, in a sample of a tissue or body fluid obtained from an otherwise identical second mammal which is not to be administered the compound. The compound can be any compound, and can be, by way of example and not by limitation, a compound with antioxidant properties or anti-inflammatory properties. The compound is administered to the first mammal in any amount considered to be effective as an antioxidant or an anti-inflammatory compound. For example, antioxidant compounds can include vitamin E and vitamin C, and can be administered in amounts ranging from about 200 to about 2,000 international units per day for vitamin E and from about 20 milligrams to about 2,000 milligrams per day for vitamin C. Also, by way of example and not by limitation, anti-inflammatory compounds can include non-steroidal anti-inflammatory drugs, such as ibuprofen administered in amounts ranging from about 200 to about 1,600 milligrams per day; aspirin administered in amounts ranging from about 80 to about 2,000 milligrams per day, and cyclooxygenase-2 inhibitors administered in amounts ranging from about 100 to about 400 milligrams per day.

After administering the compound to the mammal, the level of the isoprostane molecular marker in a sample of a tissue or body fluid obtained from the first mammal is measured. The level of the isoprostane molecular marker can be measured by any of the methods described herein, or known to the skilled artisan. The level of the isoprostane molecular marker measured in the sample obtained from the first mammal after administering the compound is then compared with either the level of the isoprostane molecular marker measured in the sample obtained from the first mammal prior to administering the compound, or with the level of the isoprostane molecular marker measured in the sample obtained from the otherwise identical second mammal which was not administered the compound.

If, as a result of the comparison described in the last paragraph, a reduced level of the isoprostane molecular marker is identified in the sample obtained from the first mammal after administration of the compound relative to either the level of the isoprostane molecular marker in the sample obtained from the first mammal prior to administering the compound, or in the sample obtained from the otherwise identical second mammal which was not administered the compound, a compound useful for the treatment of Alzheimer's disease in a mammal is identified.

Preferably, the reduced level is a level which is from about 60% to about 100% lower than the level of the isoprostane molecular marker in the sample obtained from the untreated mammal (the otherwise identical second mammal) or in the first mammal prior to administration of the compound.

The invention also includes a method of identifying an effective amount of a compound which is useful for the treatment of Alzheimer's disease in a mammal. The method comprises measuring the level of an isoprostane molecular marker for lipid peroxidation in either a sample of a tissue or body fluid obtained from a first mammal prior to administering the compound, or in a sample of a tissue or body fluid obtained from an otherwise identical second mammal which is not to be administered the compound. The compound is then administered in an amount suspected to be effective for the treatment of Alzheimer's disease to the first mammal. The compound can be any type of compound, including any of the types of compounds described herein. The amount of such compounds administered may range from about 1 nanogram per kilogram of body weight per day to about 100 milligrams per kilogram of body weight per day.

After administering the compound in the amount suspected to be effective, the level of the isoprostane molecular marker is measured in a sample of a tissue or body fluid obtained from the first mammal. The level of the isoprostane molecular marker is measured by any of the methods described herein, or by any of the methods known to the skilled artisan. The level of the isoprostane molecular marker measured in the sample obtained from the first mammal after administering the suspected effective amount of the compound is then compared with either the level of the isoprostane molecular marker measured in the sample obtained from the first mammal prior to administering the compound, or with the level of the isoprostane molecular marker measured in the sample obtained from the otherwise identical second mammal which was not administered the compound.

If, as a result of the comparison described in the last paragraph, a reduced level of the isoprostane molecular marker is identified in the sample obtained from the first mammal after administration of the suspected effective amount of the compound relative to either the level of the isoprostane molecular marker in the sample obtained from the first mammal prior to administering the compound, or in the sample obtained from the otherwise identical second mammal which was not administered the compound, an effective amount of a compound useful for the treatment of Alzheimer's disease in a mammal is identified.

Preferably, the reduced level is a level which is from about 40% to about 100% lower than the level of the isoprostane molecular marker in the sample obtained from the untreated mammal (the otherwise identical second mammal) or in the first mammal prior to administration of the compound.

The invention also includes a method of determining the optimal concentration of a compound useful for the treatment of Alzheimer's disease. The method comprises monitoring the level of an isoprostane molecular marker for lipid peroxidation in a series of mammals which are administered the compound at a series of concentrations. The concentration of the compound which results in maximal reduction of the level of the isoprostane molecular marker in one or more of the mammals without being toxic to the mammals is the optimal concentration.

In one aspect, the method is a clinical trial for the determination of the optimal concentration of a compound to be administered to a patient for the treatment of an oxidant stress syndrome or disease, for example, in the treatment of Alzheimer's disease. The level of the isoprostane molecular marker for lipid peroxidation in the series of mammals is monitored by measuring the level of the isoprostane at a series of time points using any of the methods described herein or known to the skilled artisan.

Preferably, the compound is an antioxidant compound. Another preferred compound is an anti-inflammatory compound, wherein the compound is administered at a series of concentrations effective to inhibit the activity of a cyclooxygenase enzyme in a mammal. The compound may be administered in an amount ranging from about 1 nanogram per kilogram of body weight per day to about 100 grams per kilogram of body weight per day.

Appropriate ranges for the number of mammals to be included in the series of mammals, the expected time period for duration of action of the compound, and the amount of compound to be administered are known in the art for the clinical testing of compounds which exhibit antioxidant and anti-inflammatory properties. For example, ranges for amounts of antioxidant and anti-inflammatory compounds to be administered are described herein. Preferred time periods for duration of action of both antioxidant and anti-inflammatory compounds include an overnight time period (i.e. about 8 to 12 hours) after administration of the compound and a period for spot checking the activity of a compound just after administration (i.e. about 1 to 2 hours).

By way of example, and not by limitation, some clinical situations in which the inventive methods are useful can be illustrated as follows. Alzheimer's disease is known in the art to include an inflammatory component which is susceptible to therapeutic intervention. Since the severity of the inflammatory component varies between individuals with AD and within an individual with AD over time, a physician seeking to learn whether there is a rational basis for therapeutic intervention using, for example, an antioxidant or an anti-inflammatory drug at a given point in time needs methods which assist in establishing a diagnosis of AD ante mortem and in establishing an active inflammatory process at the time of designing a clinical study and in routine medical practice. The methods of the invention are useful, for example, in non-invasive assessment of the oxidant component of inflammation in both clinical trials of new antioxidants or anti-inflammatory compounds or for use in routine medical practice to identify patients who might benefit from such drugs and as an aid to selection of the optimal concentration of drug and dosage frequency. The impact of antioxidants is likely to be inversely related to the degree of depletion of endogenous antioxidant defenses. The methods of the invention can be used, for example, to identify patients in whom oxidant stress is evident. Suppression of the inflammatory component by an antioxidant compound as measured by a method of the invention can be used to identify an effective concentration of drug for that patient, and thereafter an optimal concentration of drug.

The invention also includes a method of determining the optimal dosage frequency of a compound useful for the treatment of Alzheimer's disease. The method comprises monitoring the level of an isoprostane molecular marker for lipid peroxidation in a series of mammals administered the compound at a series of dosage frequencies. The dosage frequency which results in maximal reduction of the level of the isoprostane molecular marker in one or more of the series of mammals and which is also not toxic to the mammals is the optimal dosage frequency. In one aspect, the method is a clinical trial for the determination of the optimal dosage frequency of a compound to be administered to a patient for the treatment of an oxidant stress syndrome or disease, for example, in the treatment of Alzheimer's disease. The level of the isoprostane molecular marker for lipid peroxidation in the series of mammals is monitored by measuring the level of the isoprostane at a series of time points using any of the methods described herein or known to the skilled artisan.

Preferably, the compound is an antioxidant compound. Another preferred compound is an anti-inflammatory compound, wherein the compound is administered at a series of concentrations effective to inhibit the activity of a cyclooxygenase enzyme in a mammal.

The invention also includes a method of identifying a compound useful for reducing the level of an isoprostane molecular marker for lipid peroxidation in a sample of a tissue or body fluid obtained from a first mammal. The method comprises measuring the level of the isoprostane molecular marker in either a sample of a tissue or body fluid obtained from the first mammal prior to administering the compound, or in a sample of a tissue or body fluid obtained from an otherwise identical second mammal which is not to be administered the compound. The method also includes administering the compound to the first mammal. The compound may be any type of compound, including any of the types of compounds described herein. The compound may be administered in an amount ranging from about 1 nanogram per kilogram of body weight per day to about 100 grams per kilogram of body weight per day. After administering the compound, the level of the isoprostane molecular marker in a sample of a tissue or body fluid obtained from the first mammal is measured by any of the methods described herein, or any of the methods known to the skilled artisan.

The level of the isoprostane molecular marker measured in the sample obtained from the first mammal after administering the compound is then compared with either the level of the isoprostane molecular marker measured in the sample obtained from the first mammal prior to administering the compound, or with the level of the isoprostane molecular marker measured in the sample obtained from the otherwise identical second mammal which was not administered the compound.

If, as a result of the comparison described in the last paragraph, a reduced level of the isoprostane molecular marker is identified in the sample obtained from the first mammal after administration of the compound relative to either the level of the isoprostane molecular marker in the sample obtained from the first mammal prior to administering the compound, or in the sample obtained from the otherwise identical second mammal which was not administered the compound, a compound useful for reducing the level of an isoprostane molecular marker for lipid peroxidation in a mammal is identified. The reduced level of the isoprostane molecular marker is defined as described above.

In one embodiment, the compound is administered in an amount effective to inhibit the activity of a cyclooxygenase (COX) enzyme in the brain tissue of the mammal.

In another embodiment, the compound is administered in an amount effective to reduce the level of a reactive oxygen species (ROS) in the brain tissue of the mammal.

The invention also includes a kit for diagnosing Alzheimer's disease in a mammal. The kit comprises a sample container for containing a tissue or body fluid sample obtained from the mammal.

The kit also includes a solution useful in the extraction of an isoprostane molecular marker for lipid peroxidation from the tissue or body fluid sample obtained from the mammal. Preferably, the solution is an ethanol solution.

Also included in the kit is a negative control solution containing an isoprostane molecular marker at a concentration of about the concentration of the isoprostane molecular marker which is present in a tissue or body fluid sample of a mammal which is not afflicted with Alzheimer's disease. Preferably, the isoprostane molecular marker is suspended in an ethanol solution. Ranges for such concentrations are described herein in the Examples.

The kit also includes a positive control solution containing an isoprostane molecular marker at a concentration of about the concentration of the isoprostane molecular marker which is present in a tissue or body fluid sample of a mammal which has Alzheimer's disease. Preferably, the isoprostane molecular marker is suspended in an ethanol solution. Ranges for such concentrations are described herein in the Examples.

Additionally, the kit includes an antibody directed against an isoprostane molecular marker for lipid peroxidation. Methods for the preparation and purification of antibodies are known in the art, and are described, for example, in Harlow et al., 1988, *Antibodies: A Laboratory Manual*, Cold Spring Harbor, N.Y. The antibody can be any type of antibody known in the art.

The kit can, optionally include a secondary antibody directed against the antibody specific for the isoprostane molecule.

Furthermore, the kit includes an instructional material for use in the diagnosis of Alzheimer's disease in a mammal. The instructional material can be a publication, a recording, a diagram, or any other medium of expression which can be used to communicate the usefulness of the method of the invention in the kit for diagnosing Alzheimer's disease in a mammal. The instructional material of the kit of the invention may, for example, be affixed to a container which contains other contents of the kit, or be shipped together with a container which contains the kit. Alternatively, the instructional material may be shipped separately from the container with the intention that the instructional material and the contents of the kit be used cooperatively by the recipient.

The invention also includes a kit for measuring the level of an isoprostane molecular marker of lipid peroxidation in a tissue or body fluid sample obtained from a mammal. The kit comprises a sample container for containing a tissue or body fluid sample obtained from the mammal.

The kit also includes a solution useful in the extraction of an isoprostane molecular marker for lipid peroxidation from the tissue or body fluid sample obtained from the mammal. A preferred solution is an ethanol solution.

The kit also includes a negative control solution containing an isoprostane molecular marker at a concentration of about the concentration of the isoprostane molecular marker which is present in a tissue or body fluid sample of a mammal which is not afflicted with Alzheimer's disease. Preferably, the isoprostane molecular marker is suspended in an ethanol solution. Ranges for such concentrations are described herein in the Examples.

Also included in the kit is a positive control solution containing an isoprostane molecular marker at a concentration of about the concentration of the isoprostane molecular marker which is present in a tissue or body fluid sample of a mammal which has Alzheimer's disease. Preferably, the isoprostane molecular marker is suspended in an ethanol solution. Ranges for such concentrations are described herein in the Examples.

Additionally, the kit includes an antibody directed against an isoprostane molecular marker for lipid peroxidation. Methods for the preparation and purification of antibodies are known in the art, and are described, for example, in Harlow et al., 1988, *Antibodies: A Laboratory Manual*, Cold Spring Harbor, N.Y. The antibody can be any type of antibody known in the art.

The kit can, optionally include a secondary antibody directed against the antibody specific for the isoprostane molecule.

Furthermore, the kit includes an instructional material for use in the measurement of the level of an isoprostane molecular marker in a tissue or body fluid sample obtained from a mammal. The instructional material can be a publication, a recording, a diagram, or any other medium of expression which can be used to communicate the usefulness of the method of the invention in the kit for measurement of the level of an isoprostane molecular marker in a tissue or body fluid sample obtained from a mammal. The instructional material of the kit of the invention may, for example, be affixed to a container which contains other contents of the kit, or be shipped together with a container which contains the kit. Alternatively, the instructional material may be shipped separately from the container with the intention that the instructional material and the contents of the kit be used cooperatively by the recipient.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLE 1

In the experiments described in this Example, the levels of two isoprostanes ($iPF_2$-III and $iPF_2$-VI) were found to be increased selectively in affected regions of AD brain (i.e., frontal pole and temporal pole, but not in cerebellar cortex). Also, elevated levels of $iPF_2$-III and $iPF_2$-VI were detected in samples of AD frontal and temporal pole tissue relative to levels in samples obtained from patients with Parkinson's disease (PD), Schizophrenia (SCHI) or from brains of neurologically normal controls. Furthermore, the levels of these isoprostanes in ventricular CSF were elevated in AD brains. Thus, these studies suggested that oxidant stress plays a role in the pathogenesis of AD, and that the determination of isoprostane levels in CSF or other body fluids such as plasma and urine can be exploited to develop tests for the diagnosis of AD in living patients or for the assessment of elevated levels of lipid peroxidation in a mammal. These data also imply that the mechanism of oxidant stress in the AD brain could become a target for the design of new therapeutic compounds to arrest or slow the progression of AD in a mammal.

Preparation of Brain Tissue Samples

Brain specimens were obtained at autopsy from 19 patients with AD, 6 with PD, 10 with SCHI and 8 control subjects. The postmortem diagnostic evaluation of the patients and controls studied in these experiments was performed according to previously described procedures and criteria (Schmidt et al., 1991, Lab. Invest. 64:352–357; Arnold et al., 1995, Am. J. Psych.152:731–737; Schmidt et al., 1996, Acta Neuropathol. 91:475–481). The control subjects had no history of either dementia, other neurological disease or systemic illness affecting the brain. Neuropathologic examination failed to reveal any significant abnormalities in the control brains. One to five milligram samples of unfixed, frozen (−80° C.) frontal pole (FP), temporal pole (TP and cerebellum tissue were assessed for isoprostane levels. CSF which was clear and blood-free was obtained at autopsy from the lateral ventricle of additional AD (n=15, 10 males, 5 females, age 65–85 years old) and non-AD (n=10, 7 males, 3 females, age 67–86 years old) control brains. The CSF was centrifuged at 1,500 rpm for 10 minutes, aliquoted and stored at −80° C. until analysis. All of the CSF and brain samples were coded, so that subsequent analysis of these samples was performed without knowledge of the age or diagnosis of the individuals from whom they were obtained or the regional identity of the brain tissues.

Preparation of Brain Sample Extracts

The samples of FP, TP and cerebellum tissue were minced and resuspended in phosphate buffered saline containing 10 mM EDTA and 1 mM butylated hydroxytoluene (BHT) to prevent auto-oxidation. Ten micrograms of [$^2H_8$]-arachidonic acid were also added to the samples to enable the monitoring of artifactual formation of $F_2$-isoprostanes during sample extraction and processing. After homogenization with a blade homogenizer, total lipids were extracted with 20 milliliters of ice-cold Folch solution, chloroform/methanol (2:1, v/v). The solution was then vortexed and centrifuged at 800×g for 15 minutes at 4° C. The organic phase, which contained the extracted lipids, was dried under nitrogen, then 5 milliliters of aqueous potassium hydroxide (15%) was added and the mixture was incubated at 45° C.

for 1 hour to effect hydrolysis and release of total iPF$_2$-III and iPF$_2$-VI. Levels of 6-keto PGF$_1$ were assessed in the same specimens as described herein.

Biochemical Analysis

The levels of iPF$_2$-III and iPF$_2$-VI and 6-keto PGF$_1$ were assessed using gas chromatography/mass spectrometry assay as previously described (Praticò et al., 1995, J. Biol. Chem. 270:9800–9808; Praticò et al., 1998, Proc. Natl. Acad. Sci. USA 95:3449–3454). Briefly, known amounts of the internal standards [$^{18}O_2$]-iPF$_2$-III, [$^2H_4$]-iPF$_2$-VI or [$^2H_4$]-6-keto PGF$_1$ were added to the samples. The samples were then subjected to solid phase extraction, derivatized, and purified by two thin layer chromatography steps. Finally, each sample was analyzed for isoprostane and 6-keto PGF$_1$ content on a Fisons MD-800 (Fisons Instruments, Milan, Italy) gas chromatography/mass spectrometer, and quantification was performed using peak ratios.

Statistical Analysis

Data are presented as means±SEMs. Median values and ranges are given for iPF$_2$-III, iPF$_2$-VI and 6-keto PGF$_1$. Statistical analysis was performed by analysis of variance with subsequent pairwise comparison by 2 tailed t test, as appropriate. Only p values lower than 0.05 were regarded as statistically significant. Correlations between the two isoprostanes, the isoprostanes and the post-mortem interval (PMI), age or the duration of the disease in AD patients were examined using linear regression.

Results

The results of clinical and autopsy data on the patient and control groups are shown in Table 1. No significant difference was observed in age and PMI between the groups. The level of iPF$_2$-III in tissue samples obtained from the frontal pole (FP) of AD brains was found to be markedly elevated [median (range) pg/g wet tissue, 410 (240–880) pg/g wet tissue] relative to the level in FP brain tissue samples obtained from patients with PD [230 (80–300) pg/g wet tissue, p=0.004], patients with SCHI [280 (130–380) pg/g wet tissue, p<0.001] or normal control subjects [200 (81–260) pg/g wet tissue, p=0.002] as indicated in FIG. 1. A similar elevation in the levels of iPF$_2$-III was observed in tissue samples obtained from the temporal pole (TP) of AD patients relative to the controls. These results were [median (range) pg/g wet tissue)] as follows: for AD patients [445 (250–685)], for PD patients [303 (160–350)], for SCHI patients [223 (130–300)], and for normal controls [205 (110–300)]. No statistically significant correlation was observed between age, PMI, or disease duration and the levels of iPF$_2$-III in the FP or TP tissue samples from brains of patients with AD.

Figure 2:
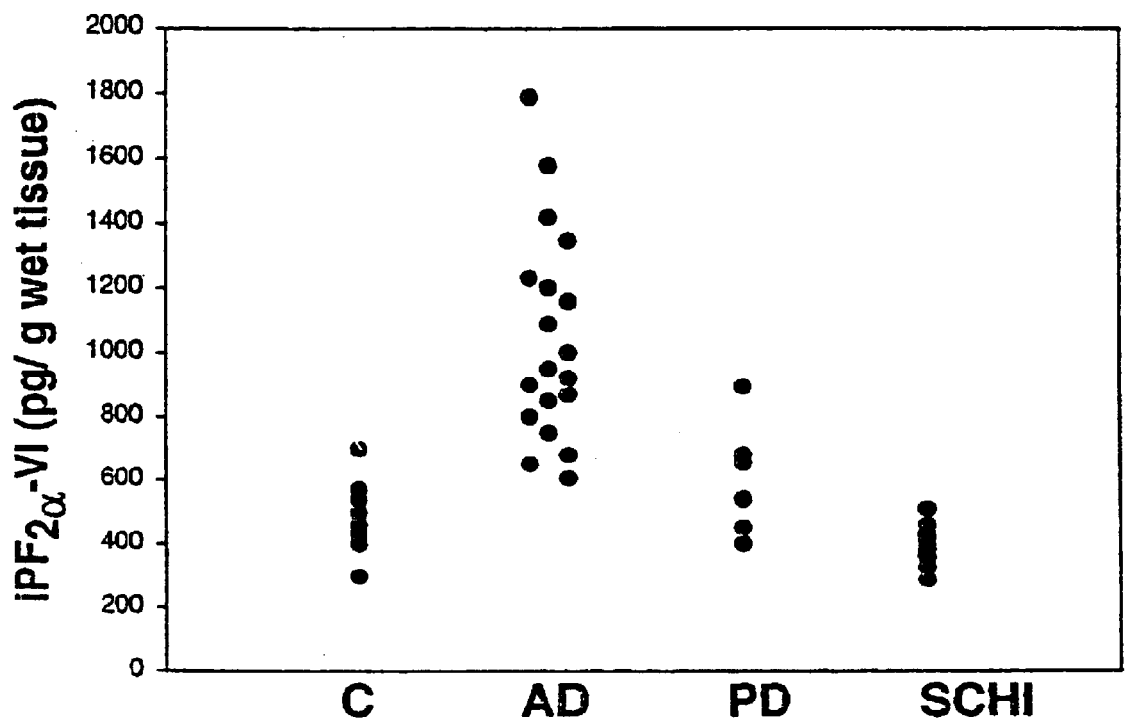
FIG. 2 is a graph depicting levels of the isoprostane $iPF_{2\alpha}$-VI in tissue samples obtained from the brain frontal pole of normal controls (C), Alzheimer's disease (AD), Parkinson's disease (PD) and Schizophrenia (SCHI) patients. The levels of $iPF_{2\alpha}$-VI are expressed in picograms per gram of wet tissue sample.
Figure 3:
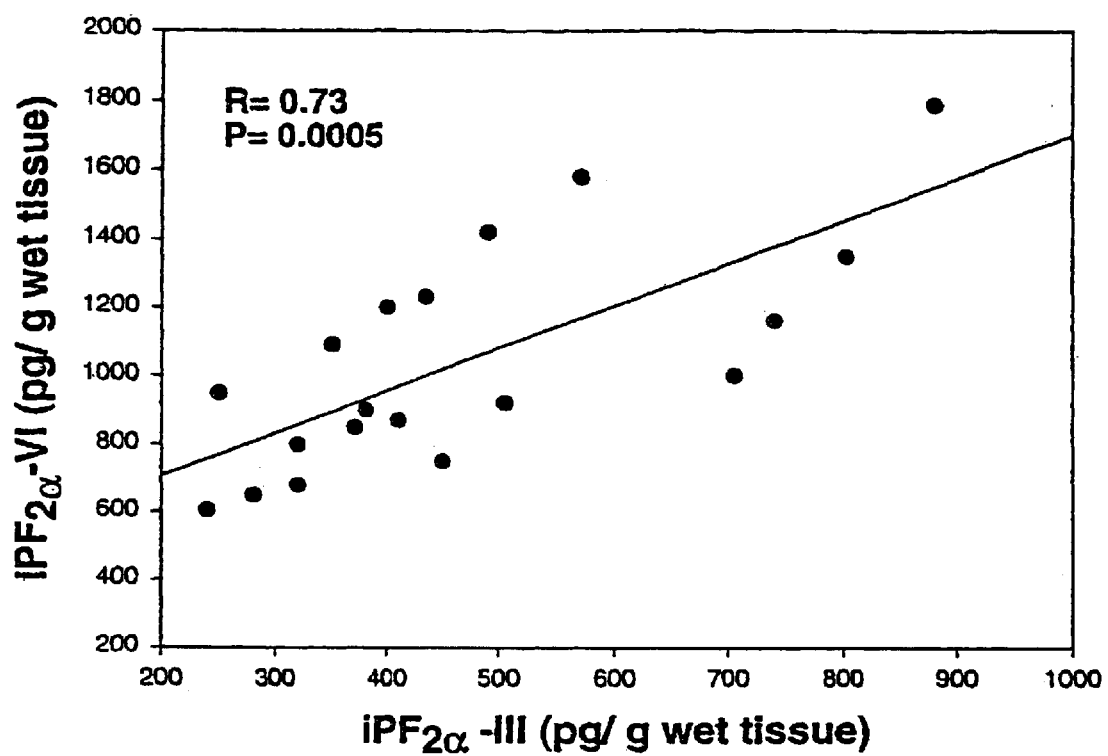
FIG. 3 is a graph depicting the correlation between the levels of the isoprostanes $iPF_{2\alpha}$-III and $iPF_{2\alpha}$-VI in tissue samples obtained from the brain frontal pole of Alzheimer's disease (AD) patients. The levels of the isoprostanes are expressed in picograms per gram of wet tissue sample.

The levels of iPF$_2$-VI in the brains of patients with AD were higher than those for iPF$_2$-III, and ranged from 605 to 1790, with a median of 950 pg/g wet tissue in the FP of AD brains. The corresponding values were 650 (400–894), (p=0.004) in PD brains; 400 (290–510), (p<0.001) in SCHI brains; and 460 (300–700), (p<0.001) pg/g wet tissue in the normal control brains, as indicated in FIG. 2. Notably, similar results were obtained from assays of the levels of iPF$_2$-VI in the TP samples where the values [median (range) pg/g wet tissue)] were [1100 (700–1880)] for AD, [700 (500–950)] for PD, [355 (220–420)] for SCHI and [480 (320–650)] for normal controls. Once again, there was no significant correlation observed between age, PMI, or disease duration and iPF$_2$-VI levels in any of these AD patients. However, there was a significant correlation between the levels of these two isoprostanes in both FP brain cortex (R=0.73, p=0.0005; FIG. 3), and TP samples from AD patients. [$^2H_8$]-arachidonic acid (10 micrograms) was incubated with the tissue at the time of the processing to determine if the postmortem procedures for isoprostane analysis artifactually produced 8-iso-PGF$_2$ or IPF$_2$-I from arachidonyl-containing phospholipids in these brain samples. There was no [$^2H_8$]-iPF$_2$-III or [$^2H_8$] iPF$_2$-VI formed during the processing procedure used herein.

The levels of the hydrolysis product of prostacyclin, prostaglandin 6-keto PGF$_1$, (a product of cyclooxygenase-dependent metabolism of arachidonic acid) were also assessed in the same samples. Notably, in sharp contrast to the isoprostanes, no difference was observed in the levels of 6-keto PGF$_1$ between the AD and non-AD control groups (see Table 2). The levels of the two F$_2$-isoprostanes were also investigated in cerebellar samples obtained from the same subjects, since the cerebellum is typically almost devoid of AD lesions. The levels of iPF$_2$-III and iPF$_2$-VI were found to be lower in cerebellum than in neocortex. Furthermore, no significant differences were observed in the levels of these F$_2$-isoprostanes when levels in AD cerebellum were compared to levels in the cerebellum of the non-AD controls (see Table 3).

Also, postmortem ventricular CSF obtained from additional AD (n=15) and non-AD controls (n=10) was assessed for levels of the two F$_2$-isoprostanes. IPF$_2$-III levels were found to be higher in AD CSF than in non-AD patients, but the difference was not found to be statistically significant [49 (30–84) vs 41 (22–60) pg/ml, p=0.14]. In contrast, iPF$_2$-VI levels were found to be significantly higher in AD CSF relative to non-AD CSF [102(33–220) vs 38 (22–80) pg/ml; p=0.009]. No correlation was observed between CSF levels of the two isoprostanes and age, PMI or disease duration.

TABLE 1

Characterization of Study Groups by Number, Male-to-Female Ratio, Age, and Postmortem Interval.

| Study group | N | Gender (M/F) | Age (year) | PMI (hour) |
|---|---|---|---|---|
| AD | 19 | 10/9 | 79 ± 2.1 (56–92) | 10.3 ± 1.4 (4–17) |
| PD | 6 | 6/0 | 68 ± 8 (34–80) | 8.7 ± 1.6 (5–15) |
| SCHI | 10 | 5/5 | 75 ± 1.2 (69–82) | 11.8 ± 1.1 (7–16.5) |
| CONTROLS | 8 | 5/3 | 76 ± 4.8 (60–98) | 11.4 ± 1.4 (5–16) |

Age, postmortem interval (PMI) are reported as means ± SEMs, ranges are given in parentheses. M/F is male-to-female ratio.

TABLE 2

6-keto PGF$_1$ Levels in frontal pole cortex of normal controls (C), Alzheimer's disease (AD), Parkinson's disease (PD) and Schizophrenia (SCHI) patients

|  | C (n = 8) | AD (n = 19) | PD (n = 6) | SCHI (n = 10) |
|---|---|---|---|---|
| 6-keto PG$_1$ (pg/g wet tissue) | 960 ± 196 (145–2300) | 703 ± 170 (100–2090) | 716 ± 171 (190–1800) | 1040 ± 230 (260–2400) |

Results are expressed as means ± SEMs. Range values are given in parentheses.

TABLE 3

IPF$_2$-III and iPF$_2$-VI levels in cerebellum from Alzheimer's disease (AD), Parkinson's disease (PD) and Schizophrenia (SCHI) patients.

| | AD (n = 19) | PD (n = 6) | SCHI (n = 10) |
|---|---|---|---|
| IPF$_2$-III (pg/g wet tissue) | 100 ± 10 (50–141) | 118 ± 12 (60–170) | 95 ± 11 (40–135) |
| IPF$_2$-VI (pg/g wet tissue) | 128 ± 9.9 (95–180) | 126 ± 10 (90–175) | 119 ± 8.7 (96–165) |

(Results are expressed as means ± SEMs. Ranges are given in parentheses.)

EXAMPLE 2

The experiments discussed in this Example describe the assessment of levels of the isoprostane molecular marker of lipid peroxidation 8,12-iso-iPF$_2$-VI in cerebrospinal fluid (CSF), plasma and urine samples obtained from human patients with a clinical diagnosis of AD as compared with healthy controls. The evidence that 8,12-iso-iPF$_2$-VI is the most abundant F$_2$ isoprostane in human urine is discussed in Lawson et al. (1998, J. Biol. Chem. 273:29295–29301). Twenty-five patients with a diagnosis of AD probable, ten with AD possible and twenty-five healthy controls were studied. Levels of 8,12-iso-iPF$_2$-VI in CSF, plasma and urine, as well as CSF tau protein, CSF Aβ$_{1-40}$, Aβ$_{1-42}$ and the apoE genotype were assayed. The results indicated that patients with a diagnosis of probable and possible AD had higher levels of 8,12-iso-iPF$_2$-VI in CSF, plasma and urine than healthy controls. A direct correlation was observed between levels of 8,12-iso-iPF$_2$-VI in CSF and plasma and between levels of 8,12-iso-iPF$_2$-VI in CSF and urine. Furthermore, CSF isoprostane levels correlated directly with CSF-tau protein and the Dementia Severity Rating Scale (DSRS) and inversely with the percentage of CSF Aβ-$_{1-42}$ and the Mini Mental State Examination (MMSE). AD patients homozygous for apoE ϵ4 allele had higher isoprostane levels than patients without the apoE ϵ4 allele or with one copy of the apoE ϵ4 allele.

The results of these experiments suggest that patients with a clinical diagnosis of AD exhibit in vivo increased lipid peroxidation levels in CSF, plasma and urine early in the course of the disease. The correlation observed between increased lipid peroxidation levels and other risk factors of the disease suggests that the non-invasive approach described herein can be used to identify AD patients for whom antioxidant therapy may be efficacious. The present studies provide evidence that isoprostane levels are elevated in AD patients compared to healthy individuals not only in CSF but also in plasma and urine, and levels of the isoprostane 8,12-iso-iPF$_2$-VI correlates with other markers and risk factors known in the art for AD. Furthermore, the correlation of levels of the isoprostane 8,12-iso-iPF$_2$-VI in urine with levels of the isoprostane in CSF indicates that non-invasive measurement of this molecular marker for lipid peroxidation in urine will reflect levels of oxidant stress in the brain.

The materials and methods used in these experiments were as follows.

Selection of Patients

Subjects were recruited from the Memory Disorders Clinic (MDC) at the University of Pennsylvania (Philadelphia, Pa.). Informed consent was obtained from all participants to the study. The clinical diagnosis of probable or possible AD was based on the National Institute of Neurological and Communicative Diseases and Stroke-Alzheimer's Disease and Related Disorders Association criteria (Radebaugh et al., 1996, Alzheimer's Disease & Associated Disorders 10 Supp 1: 15). As part of their routine cognitive assessment, all patients received the Consortium to Establish a Registry for Alzheimer's Disease (CERAD) psychometric battery for the assessment of memory, language and praxis. The Dementia Severity Rating Scale (DSRS) and the Mini Mental State Examination (MMSE) were performed to evaluate the clinical severity of the disease. Extensive laboratory studies were performed as well as magnetic resonance imaging and single-photon emission computed tomography in order to exclude other disorders of dementia. Patients with any other medical condition that could explain the dementia, including multiple infarct states, were excluded from the study. Subjects were excluded from the study if they had an acute infectious or inflammatory disease, hepatic chronic disease, alcoholism, cancer, estrogen replacement therapy or were treated with vitamins.

Twenty-five patients were enrolled in the study, and urine and blood samples were obtained from each patient. Two weeks after taking this sample, samples of CSF were obtained from a subgroup of the population study using lumbar puncture. An additional urine sample was collected along with the collection of the CSF sample. Control subjects were from the Alzheimer's Disease Center cognitively normal cohort and from spouses of patients attending the MDC.

Preparation of Samples for Isoprostane Analysis

Urine, plasma and CSF were collected into tubes containing 0.1% of the antioxidant butylated hydroxytoluene and stored at −80° C. until analysis. Samples were spiked with internal standard [$^4$H$_2$]-8,12-iso-iPF$_2$-VI, extracted on a solid phase extraction column, purified by thin layer chromatography and assayed using negative ion chemical ionization gas chromatography/mass spectrometry (GC/MS) as described below and as described by Pratico et al. (1998, Nature Med., 4:1189–1192; and 1999, Atheroscler. 147:1–10). The intra-assay and inter-assay variability for this method was ±4% and 5%, ±4.5% and 4% for urine and plasma, respectively. Urinary isoprostane (iP) levels are expressed as nanograms per milligram of creatine. Blood, anticoagulated with EDTA, was immediately centrifuged at 3,000 rpm for 15 minutes at 4° C. to obtain plasma and stored at −80° C. Prior to analysis, plasma was treated as described above. Isoprostane levels in plasma are expressed as picograms per milliliter plasma. CSF was collected visually free of blood contamination, sedimented at 1,500 rpm for 15 minutes and then an aliquot (1 milliliter) was frozen immediately at −80° C. Isoprostane levels in CSF are expressed as picograms per milliliter of CSF. All assays were performed in a coded fashion.

Gas Chromatography/Mass Spectrometry Assay

Gas chromatography/mass spectrometry assays (GC/MS) were performed using synthetic homologous standards, unlike previously published methods, in which the analyte and the internal standard are heterologous. Homologous standards were synthesized and prepared as previously reported by Hwang et al. (1994, J. Am. Chem. Soc. 116:10829–10830) and Pudukulathan et al. (1998, J. Am. Chem. Soc. 120:11953–11961). Using the homologous standards, assay conditions were developed as described herein which enabled the quantitation of a single isoprostane isomer.

Since iPF$_2$-III was reported to be a prominent F$_2$-iP which had bioactivity in vitro and in vivo, (Banerjee et al., 1992, Am. J. Physiol. 263:H660-H663; Takahashi et al., 1992, J. Clin. Invest. 90:136–141) initial development of the GC/MS assay focused on this isoprostane. An assay was developed which measured a single isoprostane isomer by synthesizing [$^{18}O_2$]iPF$_2$-III and improving the GC/MS characteristics by using the tert-butyldimethylsilyl ether instead of the trimethylsilyl ether (Pratico et al., 1995, J. Biol. Chem 270:9800–9808). This assay, which included one solid phase extraction step, two thin layer chromatography steps, and two derivatizations, was technically demanding. Since iPF$_2$-III, unlike other F$_2$ isoprostanes, can be formed by either the COX-1 or the COX-2 enzyme (Pratico et al., 1995, J. Biol. Chem 270:9800–9808; Pratico et al., 1996, J. Biol. Chem 271:8919–8924), this potentially undermined the value of using iPF$_2$-III as an index of lipid peroxidation in vitro. Therefore, the isoprostane iPF$_2$-VI (formerly known as iPF$_2$-I) was used instead in the development of this assay (Adiyaman et al., 1996, Tetrahedron Lett. 37:4849–4852). The isoprostane iPF$_2$-VI was promising as a target analyte because it can readily be converted to a cyclic lactone, enabling facile separation of this isoprostane isomer from other F$_2$ isoprostanes of classes III, IV, and V. Also, iPF$_2$-VI is present in urine at concentrations higher than iPF$_2$-III and iPF$_2$-VI is not generated by a COX enzyme-dependent manner (Pratico et al., 1998, Proc. Natl. Acad. Sci. U.S.A. 95:3449–3454).

Measurement of CSF-tau, CSF Aβ$_{1-40}$, and Aβ$_{1-42}$

Tau protein levels were measured using a sandwich-ELISA method using the Innotest hTAU-Antigen kit (Innogenetics, Zwijndrecht, Belgium) (Arai et al., 1995, Ann. Neurol. 38:649–652). Aβ-$_{1-40}$ and Aβ$_{1-42}$ levels were measured using a sandwich-ELISA method using monoclonal antibodies specific for different species of Aβ (Turner et al., 1996, J. Biol. Chem. 271:8966–8970). Synthetic Aβ$_{1-40}$ and Aβ-$_{1-42}$ peptides (Bachem) were used to generate standard curves. The sandwich-ELISA method had a detection limit of <1 femtomole of synthetic Aβ per sample. All assays were performed in a coded fashion.

Assessment of ApoE Genotype

DNA was extracted from peripheral leukocytes and ApoE genotyping was performed as described in (Wenham et al., 1991, Lancet 337:1158–1159) without knowledge of the clinical diagnosis of the patient. Briefly, a one-stage polymerase chain reaction was performed after isolating the DNA. This technique has been demonstrated to be very efficient and specific even for routine purposes (Petersen et al., 1995, JAMA 273(16):1274–8).

Statistical Analysis

Comparisons among groups were performed using non-parametric one-way analysis of variance (Kruskall-Wallis test) with the use of Dunn's post-test. Correlation was studied using linear regression analysis. Statistical significance was set at p<0.05.

Results

Figure 4:
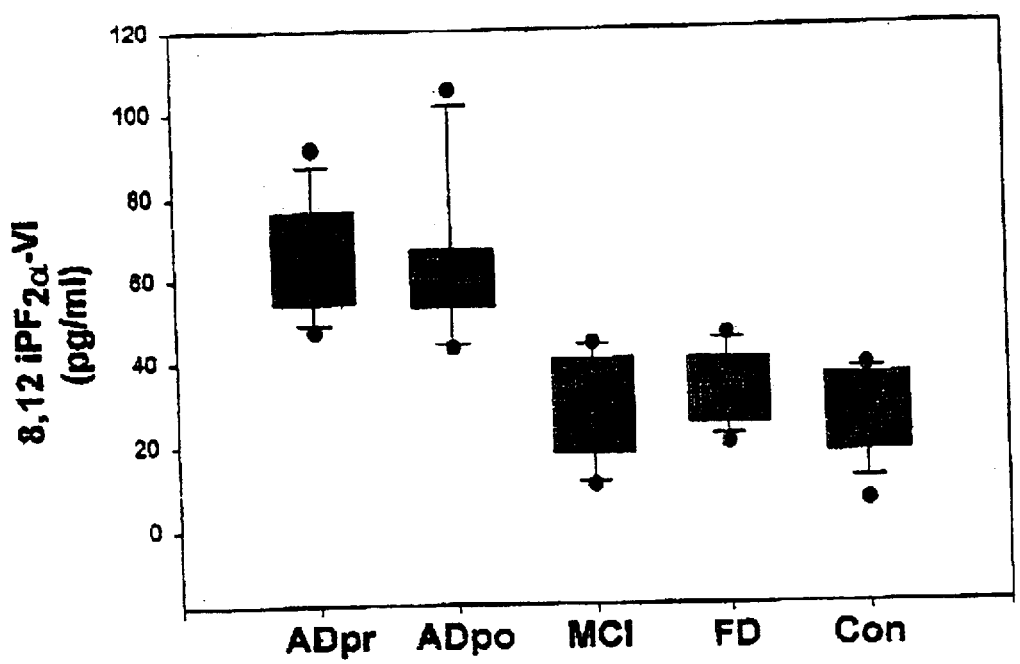
FIG. 4 is a graph depicting levels of 8,12-iso-$iPF_{2\alpha}$-VI in CSF obtained from living human patients with a probable (ADpr) or possible (ADpo) diagnosis of AD. Control groups include patients with Mild Cognitive Impairment (MCI), Frontal Dementia (FD) and healthy age-matched control (Con) patients. The levels of the isoprostane are expressed in picograms per milliliter.
Figure 5:
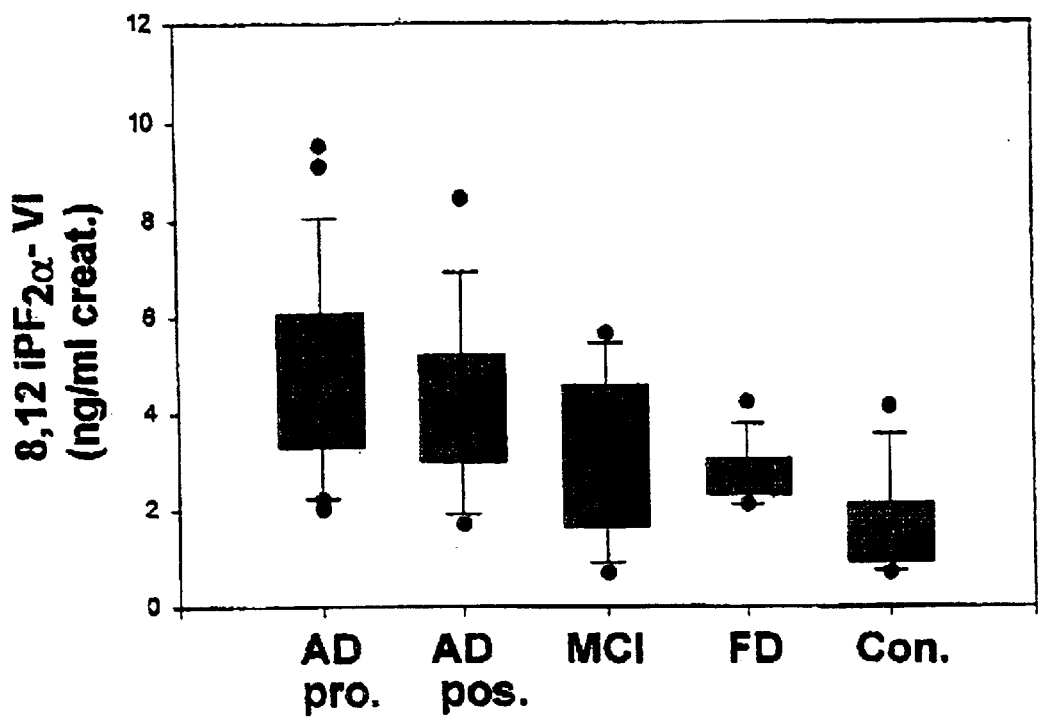
FIG. 5 is a graph depicting levels of 8,12-iso-$iPF_{2\alpha}$-VI in urine obtained from living human patients with a probable (ADpro.) or possible (ADpos.) diagnosis of AD. Control groups include patients with Mild Cognitive Impairment (MCI), Frontal Dementia (FD) and healthy age-matched control (Con) patients. The levels of the isoprostane are expressed in nanograms per milliliter.
Figure 6:
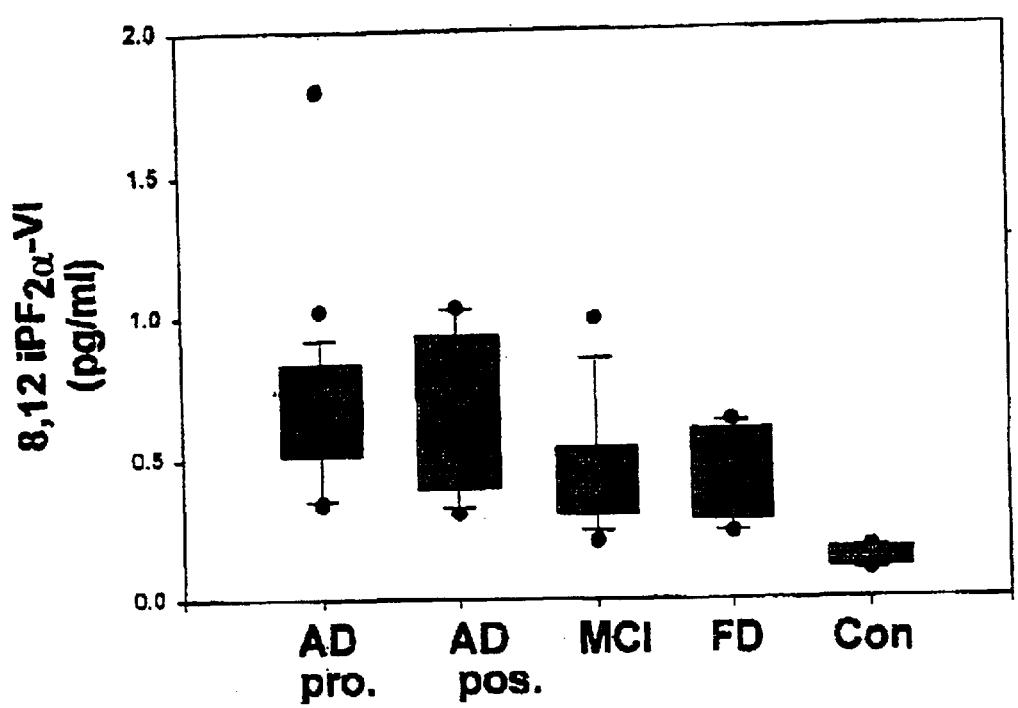
FIG. 6 is a graph depicting levels of 8,12-iso-$iPF_{2\alpha}$-VI in plasma obtained from living human patients with a probable (ADpro.) or possible (ADpos.) diagnosis of AD. Control groups include patients with Mild Cognitive Impairment (MCI), Frontal Dementia (FD) and healthy age-matched control (Con) patients. The levels of the isoprostane are expressed in picograms per milliliter.
Figure 7A:
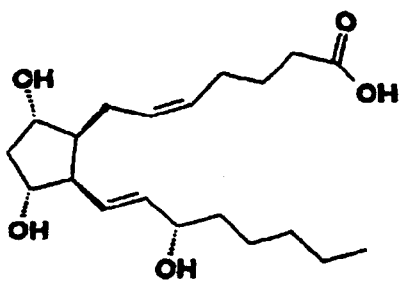
FIGS. 7A, 7B, and 7C is a series of formulae depicting the chemical structure of the isoprostanes $iPF_{2\alpha}$-III, $iPF_{2\alpha}$-VI and 8,12-iso-$iPF_{2\alpha}$-VI, respectively.
Figure 7B:
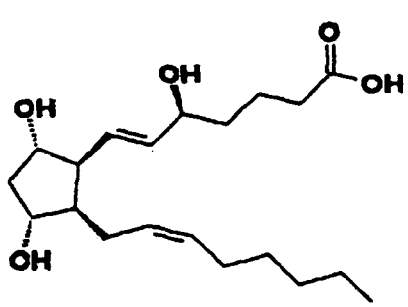
Figure 7C:
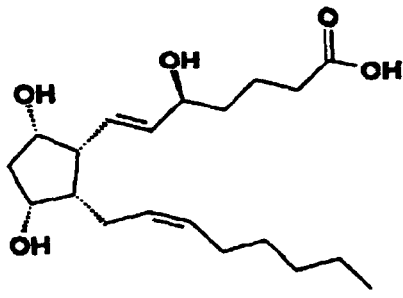

The characteristics of the patients diagnosed with probable AD and possible AD according to the NINCDS-ADRDA criteria as well as the characteristics of control subjects are shown in Table 4. In control subjects, levels in urine of 8,12-iso-iPF$_2$-VI ranged from between 0.75 and 4.1 nanograms per milligram of creatine as depicted in FIG. 5, and plasma levels of 8,12-iso-iPF$_2$-VI ranged from between 0.1 and 0.2 picograms per milliliter as depicted in FIG. 6. In patients with a clinical diagnosis of AD probable, urine and plasma levels of 8,12-iso-iPF$_2$-VI were greater than in controls (p<0.0001, for both) as depicted in FIGS. 5 and 6. A similar pattern was observed in patients with a clinical diagnosis of AD possible as depicted in FIGS. 5 and 6. CSF was obtained from a subgroup of the population study comprised of ten subjects with a diagnosis of AD probable, four subjects with a diagnosis of AD possible and ten control subjects. Along with the collection of the CSF sample, a second urine sample was also collected. Levels of 8,12-iso-iPF$_2$-VI measured in these urine samples did not differ significantly from the ones obtained initially at baseline. In control subjects, levels in CSF of 8,12-iso-iPF$_2$-VI ranged from between 6 and 38 picograms per milliliter as depicted in FIG. 4. In subjects with a diagnosis of AD probable and AD possible, levels of 8,12-iso-iPF$_2$-VI were significantly higher, and ranged from between 47 and 91 picograms per milliliter (p<0.0001), and from between 43 and 105 pg/ml (p<0.0001), respectively, as depicted in FIG. 4. A direct correlation was observed between levels of 8,12-iso-iPF$_2$-VI in urine and in CSF ($r^2$=0.55, p<0.001) and between levels of 8,12-iso-iPF$_2$-VI in plasma and in CSF ($r^2$=0.64, p<0.001).

Levels of CSF tau protein were also elevated in AD probable and AD possible patients relative to the control subjects as depicted in Table 5. In contrast, the percentage ratio between CSF Aβ$_{1-40}$ and Aβ$_{1-42}$ was lower in AD probable and AD possible patients relative to the control subjects (Table 5). A significant direct correlation was observed between levels of CSF tau protein and levels of 8,12-iso-iPF$_2$-VI in CSF ($r^2$=0.43, p<0.0001), whereas an inverse correlation was observed between CSF percentage of Aβ-$_{1-42}$ and levels of 8,12-iso-iPF$_2$-VI in CSF ($r^2$=−0.25, p<0.03).

In order to investigate the influence of the apoE genotype on the elevated isoprostane levels observed in CSF, subjects were grouped by the number of copies they had of the ε4 allele of the apoE. Subjects which had two copies (homozygous) of the ε4 allele were found to have significantly higher levels of 8,12-iso-iPF$_2$-VI in CSF than in subjects which had no copies or one copy (heterozygous) of the ε4 allele (p=0.04). No such correlation was found between CSF tau protein levels and the number of copies of the ε4 allele.

Finally, a direct correlation was observed between the results of two of the most common cognitive tests used to assess clinically the degree of dementia in AD patients (the Dementia Severity Rating Scale {DSRD} and the Mini Mental State Examination {MMSE}). A direct correlation was observed between DSRD results and levels of 8,12-iso-iPF$_2$-VI in CSF ($r^2$=0.22, p=0.02), whereas an inverse correlation was observed between MMSE results and levels of 8,12-iso-iPF$_2$-VI in CSF ($r^2$=−0.15, p=0.04).

Discussion of Results

The results of these experiments provide evidence that patients with a clinical diagnosis of AD (i.e., AD possible and AD probable) have elevated levels of 8,12-iso-iPF$_2$-VI, a reliable molecular marker for in vivo lipid peroxidation, in CSF, plasma and urine relative to healthy controls. The finding that the levels of this isoprostane in both plasma and urine correlated with levels of this isoprostane in CSF further indicates that oxidant stress is an early event in AD which might contribute to the evolution of the disease. Furthermore, the methods of the invention represent the first non-invasive approach to the study of lipid peroxidation levels in AD. Lipid peroxidation and oxidant stress have been widely recognized in the art as possible pathogenic mechanisms in AD.

Several previous studies have demonstrated that elevated CSF tau levels reflect the progressive death of neurons in the AD brain and that elevated CSF tau levels may prove to be a reliable and early diagnostic test for AD (Tato et al., 1995, J. Neurol. Neurosurg. Psychiatry 59:280–283; Kanai et al., 1998, Ann. Neurol. 44:17–26). By contrast, CSF $A\beta_{1-42}$ levels have previously been reported to decrease with the progression of the disease, most likely due to the preferential sequestration of $A\beta_{1-42}$ as insoluble deposits in brain tissue (Nakamura et al., 1994, Ann. Neurol 36:903–911; Corder et al., 1993, Science 261:921–923).

In the experiments described in this Example, a direct correlation was demonstrated between levels of CSF tau protein and levels of 8,12-iso-iPF$_2$-VI in CSF, and an inverse correlation was demonstrated between levels of CSF $A\beta_{1-42}$ and levels of 8,12-iso-iPF$_2$-VI in CSF. Taken together, these findings indicate that in AD patients, isoprostane molecular markers for lipid peroxidation reflect an increase in CNS oxidant stress which directly correlates with the progression of the disease. The fact that isoprostane levels correlate with the progression of the disease was further corroborated by the correlation observed between levels of 8,12-iso-iPF$_2$-VI in CSF and the results of the cognitive tests discussed, since CSF levels of this isoprostane directly correlated with DSRD scores and inversely correlated with the MMSE scores.

The risk of developing sporadic AD has previously been linked to the polymorphism of the human apolipoprotein E (ApoE). Independent studies have found that the 4 allele of human apoE is present in higher copy number in AD patients relative to matched controls (Mayeux et al., 1993, Ann. Neurol 34:752–754; Van Duijin et al., 1994, Nature Genet. 7:74–78). The results of the experiments in this Example indicated a direct correlation between isoprostane levels in CSF and the copy number of the apoE 4 allele. These findings provide evidence that apoE isoforms influence the response to injury in the brain (Mahley et al., 1995, Curr. Opin. Lipidol. 6:86–91; Pratico et al., 1999, J. Neurochem. 73:736–741). Thus, specific isoforms of apoE might modulate levels of lipid peroxidation in the brain by mechanisms yet to be elucidated.

Since the neurological pathological changes of AD usually commence years before any clinical diagnosis of the disease can be made, the identification of molecular markers for lipid peroxidation which can be used for the detection of AD at an early stage is an important goal. The use of such molecular markers can facilitate the commencement of treatment of AD as early as possible in order to delay the onset of AD symptoms. The fact that no overlap was observed between levels of 8,12-iso-iPF$_2$-VI in CSF obtained from AD patients and controls strongly suggests that quantification of this isoprostane is particularly useful in the early detection of mild forms of AD. Moreover, the detection of elevated levels of isoprostanes by the methods of the present invention can be used as the rational basis for subject selection in future clinical trials for assessing the efficacy of therapeutic compounds such as antioxidants and anti-inflammatory compounds to alleviate a symptom of or delay the progression of AD.

TABLE 4

Characteristics of Patient and Control Subjects.

|  | Probable AD (n = 25) | Possible AD (n = 10) | Controls (n = 25) |
|---|---|---|---|
| Age (yr) |  |  |  |
| Mean | 76 | 75 | 74.5 |
| Range | 58–97 | 68–90 | 57–94 |
| F/M | 23/2 | 7/3 | 18/6 |

TABLE 4-continued

Characteristics of Patient and Control Subjects.

|  | Probable AD (n = 25) | Possible AD (n = 10) | Controls (n = 25) |
|---|---|---|---|
| % Caucasian | 80 | 70 | 100 |
| Education (% < 9 yr) | 2 | 1 | 0 |
| Smokers | 4 | 2 | 0 |

F/M, female to male ratio.

TABLE 5

CSF tau Protein Levels and CSF $A\beta_{1-42}$ Percentage in AD Patients and Control Subjects.

|  | AD (n = 14) | Controls (n = 10) |
|---|---|---|
| CSF tau (pg/ml) | 770<br>300–1500 | 320<br>170–460 |
| CSF $A\beta_{1-42}$ (%) | 5.3<br>2.4–7.8 | 8.0<br>5.4–16.7 |

(Results are expressed as mean and range.)

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of measuring the level of lipid peroxidation in a mammal suspected of having an oxidant stress syndrome or disease, wherein said oxidant stress syndrome or disease is Alzheimer's disease, said method comprising a) obtaining a first sample of a tissue or body fluid from said mammal;

b) assessing the level of an isoprostane molecular marker for lipid peroxidation present in said first sample, wherein said isoprotane molecular marker is selected from the group consisting of iPF$_{2\alpha}$-III, iPF$_{2\alpha}$-VI, and 8,12-iso-iPF$_{2\alpha}$-VI; and c) comparing the level of said isoprostane molecular marker present in said first sample with the level of said isoprostane molecular marker present in a second sample of a tissue or body fluid obtained from an otherwise identical mammal which is not afflicted with an oxidant stress syndrome or disease, wherein an elevated level of said isoprostane molecular marker in said first sample relative to the level of said isoprostane molecular marker in said second sample, is indicative of an elevated level of lipid peroxidation in said mammal, thereby indicating the presence of an oxidant stress syndrome or disease in said mammal.

2. The method of claim 1, further comprising after a) and prior to b) isolating from said first sample said isoprostane molecular marker.

3. The method of claim 1, wherein said elevated level of lipid peroxidation comprises an elevated level of a reactive oxygen species (ROS).

4. The method of claim 1, wherein said elevated level of lipid peroxidation comprises an elevated level of inflammation.

5. The method of claim 4, wherein said elevated level of inflammation comprises elevated cyclooxygenase (COX) activity.

6. The method of claim 1, wherein said tissue is brain tissue.

7. The method of claim 6, wherein said brain tissue is selected from the group consisting of brain frontal pole tissue and brain temporal pole tissue.

8. The method of claim 1, wherein said body fluid is selected from the group consisting of cerebrospinal fluid (CSF), plasma and urine.

9. A method of diagnosing an oxidant stress syndrome or disease in a mammal, wherein said oxidant stress syndrome or disease is Alzheimer's disease, said method comprising
   a) obtaining a first sample of a tissue or body fluid from said mammal;
   b) assessing the level of said isoprostane molecular marker present in said first sample; and wherein said isoprotane molecular marker is selected from the group consisting of $iPF_2$-III, $iPF_{2\alpha}$-VI, and 8,12-iso-$iPF_{2\alpha}$-VI; and
   c) comparing the level of said isoprostane molecular marker present in said first sample with the level of said isoprostane molecular marker present in a second sample of a tissue or body fluid obtained from an otherwise identical mammal which is not afflicted with said oxidant stress syndrome or disease, wherein an elevated level of said isoprostane molecular marker in said first sample relative to the level of said isoprostane molecular marker in said second sample, is indicative of an elevated level of lipid peroxidation in said mammal, whereby said oxidant stress syndrome or disease is diagnosed in said mammal.

10. The method of claim 9, further comprising, after a) and before b) isolating from said first sample said isoprostane molecular marker.

11. A method of measuring the level of an isoprostane molecular marker for lipid peroxidation in a mammal suspected of having an oxidant stress syndrome or disease, said method comprising
   a) obtaining a sample of a tissue or body fluid from said mammal;
   b) isolating from said sample said isoprostane molecular marker by using a total lipids solvent extraction method; and
   c) quantifying the level of said isoprostane molecular marker.

12. The method of claim 11, wherein said assaying comprises using a gas chromatography/mass spectrometry assay method which comprises a synthetic homologous isoprostane standard, and further wherein said quantifying is performed using peak area or peak height ratios.

13. The method of claim 11, wherein said oxidant stress disease is Alzheimer's disease.

14. The method of claim 11, wherein said isoprostane molecular marker is selected from the group consisting of $iPF_{2\alpha}$-III, $iPF_{2\alpha}$-VI and 8,12-iso-$iPF_{2\alpha}$-VI.

15. The method of claim 11, wherein said tissue is brain tissue.

16. The method of claim 15, wherein said brain tissue is selected from the group consisting of brain frontal pole tissue and brain temporal pole tissue.

17. The method of claim 11, wherein said body fluid is selected from the group consisting of cerebrospinal fluid (CSF), plasma and urine.

18. A method of identifying a compound useful for the treatment of Alzheimer's disease in a mammal, said method comprising
   a) measuring the level of an isoprostane molecular marker for lipid peroxidation in either a sample of a tissue or body fluid obtained from a first mammal prior to administering said compound, or, in a sample of a tissue or body fluid obtained from an otherwise identical second mammal which is not to be administered said compound;
   b) administering said compound to said first mammal;
   c) thereafter measuring the level of said isoprostane molecular marker in a tissue or body fluid obtained from said first mammal; and
   d) comparing the level of said isoprostane molecular marker measured in c) with the level of said isoprostane molecular marker measured in a), wherein when the level of said isoprostane molecular marker measured in c) is reduced relative to the level of said isoprostane molecular marker measured in a), a compound useful for the treatment of Alzheimer's disease in a mammal is identified.

19. The method of claim 18, wherein said isoprostane molecular marker of lipid peroxidation is selected from the group consisting of $iPF_{2\alpha}$-III, $iPF_{2\alpha}$-VI and 8,12-iso-$iPF_{2\alpha}$-VI.

20. The method of claim 18, wherein said tissue is brain tissue selected from the group consisting of brain frontal pole tissue and brain temporal pole tissue.

21. The method of claim 18, wherein said body fluid is selected from the group consisting of cerebrospinal fluid (CSF), plasma and urine.

22. A method of identifying an effective amount of a compound useful for the treatment of Alzheimer's disease in a mammal, said method comprising
   a) measuring the level of an isoprostane molecular marker for lipid peroxidation in either a sample of a tissue or body fluid obtained from a first mammal prior to administering said compound, or, in a sample of a tissue or body fluid obtained from an otherwise identical second mammal which is not to be administered said compound;
   b) administering to said first mammal an amount of said compound;
   c) thereafter measuring the level of said isoprostane molecular marker in a tissue or body fluid obtained from said first mammal; and
   d) comparing the level of said isoprostane molecular marker measured in c) with the level of said isoprostane molecular marker measured in a), wherein when the level of said isoprostane molecular marker measured in c) is reduced relative to the level of said isoprostane molecular marker measured in a), an effective amount of a compound useful for the treatment of Alzheimer's disease in a mammal is identified.

23. A method of determining the optimal concentration of a compound useful for the treatment of Alzheimer's disease, said method comprising monitoring the level of an isoprostane molecular marker for lipid peroxidation in a series of mammals administered said compound at a series of concentrations of compound, wherein the concentration of said compound which results in maximal reduction of the level of said isoprostane molecular marker in one or more of said series of mammals, which concentration is not toxic to said mammals, is said optimal concentration.

24. The method of claim 23, wherein said compound is an antioxidant compound.

25. The method of claim 23, wherein said compound is an anti-inflammatory compound, wherein said compound is administered at a series of concentrations effective to inhibit the activity of a cyclooxygenase (COX) enzyme in a mammal.

26. A method of determining the optimal dosage frequency of a compound useful for the treatment of Alzheimer's disease, said method comprising monitoring the level of an isoprostane molecular marker for lipid peroxidation in a series of mammals administered said compound at a series of dosage frequencies, wherein the dosage frequency of said compound which results in maximal reduction of the level of said isoprostane molecular marker in one or more of said series of mammals, which dosage is not toxic to said mammals, is said optimal dosage frequency.

27. A method of identifying a compound useful for reducing the level of an isoprostane molecular marker for lipid peroxidation in a sample of a tissue or body fluid obtained from a first mammal, said method comprising a) measuring the level of said isoprostane molecular marker in either a sample of a tissue or body fluid obtained from said first mammal prior to administering said compound, or, in a sample of a tissue or body fluid obtained from an otherwise identical second mammal which is not to be administered said compound;

b) administering said compound to said first mammal;

c) thereafter measuring the level of said isoprostane molecular marker in a tissue or body fluid sample obtained from said first mammal;

d) comparing the level of said isoprostane molecular marker measured in c) with the level of said isoprostane molecular marker measured in a), wherein when the level of said isoprostane molecular marker measured in c) is reduced relative to the level of said isoprostane molecular marker measured in a), a compound useful for reducing the level of an isoprostane molecular marker in a mammal is identified.

28. The method of claim 27, wherein said compound is present in an amount effective to inhibit the activity of a cyclooxygenase enzyme in the brain tissue of said mammal.

29. The method of claim 27, wherein said compound is present in an amount effective to reduce the level of a reactive oxygen species in the brain tissue of said mammal.

30. The method of claim 27, wherein said isoprostane molecular marker of lipid peroxidation is selected from the group consisting of $iPF_{2\alpha}$-III, $iPF_{2\alpha}$-VI and 8,12-iso-$iPF_{2\alpha}$-VI.

31. A kit for diagnosing Alzheimer's disease in a mammal, said kit comprising a) a sample container for carrying a tissue or body fluid sample from said mammal;

b) a solution for use in extraction of an isoprostane molecular marker for lipid peroxidation from said tissue or body fluid sample obtained from said mammal;

c) a negative control solution of said isoprostane molecular marker of lipid peroxidation present at a concentration of about the concentration of said isoprostane molecular marker present in a tissue or body fluid sample of a mammal which is not afflicted with Alzheimer's disease;

d) a positive control solution of said isoprostane molecular marker of lipid peroxidation present at a concentration of about the concentration of said isoprostane molecular marker in a tissue or body fluid sample of a mammal which is afflicted with Alzheimer's disease;

e) an antibody directed against an isoprostane molecular marker for lipid peroxidation; and f) an instructional material.

32. A kit for measuring the level of an isoprostane molecular marker for lipid peroxidation in a tissue or body fluid sample obtained from a mammal, said kit comprising a) a sample container for carrying a tissue or body fluid sample from said mammal;

b) a solution for use in extraction of an isoprostane molecular marker of lipid peroxidation from said tissue or body fluid sample obtained from said mammal;

c) a negative control solution of said isoprostane molecular marker of lipid peroxidation present at a concentration of about the concentration of said isoprostane molecular marker present in a tissue or body fluid sample of a mammal which is not afflicted with Alzheimer's disease;

d) a positive control solution of said isoprostane molecular marker of lipid peroxidation present at a concentration of about the concentration of said isoprostane molecular marker in a tissue or body fluid sample of a mammal which is afflicted with Alzheimer's disease;

e) an antibody directed against an isoprostane molecular marker for lipid peroxidation; and f) an instructional material.

* * * * *